(12) United States Patent
Itoh et al.

(10) Patent No.: US 6,407,129 B1
(45) Date of Patent: Jun. 18, 2002

(54) AZOLE COMPOUNDS, THEIR PRODUCTION AND THEIR USE

(75) Inventors: Katsumi Itoh, Osaka; Tomoyuki Kitazaki, Kobe; Kenji Okonogi, Osaka, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/381,479
(22) PCT Filed: Mar. 30, 1998
(86) PCT No.: PCT/JP98/01441
§ 371 (c)(1),
(2), (4) Date: Sep. 20, 1999
(87) PCT Pub. No.: WO98/43970
PCT Pub. Date: Oct. 8, 1998

(30) Foreign Application Priority Data

| Mar. 31, 1997 | (JP) | 9-080863 |
| Jul. 8, 1997 | (JP) | 9-182395 |
| Dec. 8, 1997 | (JP) | 9-337299 |

(51) Int. Cl.$^7$ .................. A61K 31/41; A61K 31/4196; C07D 403/14
(52) U.S. Cl. ...................... 514/381; 548/253
(58) Field of Search .......... 548/253; 514/381

(56) References Cited

U.S. PATENT DOCUMENTS

| 4,061,722 A | 12/1977 | Bodor |
| 4,160,099 A | 7/1979 | Bodor |
| 5,371,100 A | 12/1994 | Itoh et al. |
| 5,371,101 A | 12/1994 | Itoh et al. |
| 5,495,024 A | 2/1996 | Itoh et al. |
| 5,545,652 A | 8/1996 | Itoh et al. |
| 5,792,780 A | 8/1998 | Itoh et al. |
| 6,034,248 A | * 3/2000 | Itoh et al. ............ 548/253 |

FOREIGN PATENT DOCUMENTS

| EP | 0 567 982 A | 11/1993 |
| EP | 0 657 449 A | 6/1995 |
| EP | 0 829 478 A2 | 3/1998 |
| WO | WO 96 25410 A | 8/1996 |

OTHER PUBLICATIONS

B. Darvas et al., "Inhibitory effect of an in vivo activated . . . " Entomol. Exp. Appl. 1987, (44), pp. 295–301.
N. Bodor et al., "Soft Drugs. 1, Labile Quaternary Ammonium Salts as . . . " J. Med. Chem., 1980 (23), pp. 469–474.
N. Bodor et al., "Soft Drugs. 3. A New Class of Anticholinergic Agents" J. Med. Chem., 1980 (23), pp. 474–480.
N. Bodor et al., "Soft Drugs. 2. Soft Alkylating Compounds . . . " J. Med. Chem. 1980 (23), pp. 566–569.
P. Druzgala et al., "New Water–Soluble Pilocarpine Derivatives with . . . " Pharm. Research., (9–3) 1992 pp. 372–377.
C. Bedford. et al., "Quaternary Salts of 2–[(Hydroxyimino)methyl]imidazole . . . " J. Med. Chem., 1989, (32), pp. 493–503.
V. Massonneau et al., "Synthesis of cyclic sulfates . . . " New J. Chem. 1992, 161(1–2), 107–112.
J.C. Emmett et al., "The Synthesis of N$^\pi$–Alkylhistamines" J. Chem. Soc., Perkin Trans. 1, 1341–44 (1979).

* cited by examiner

*Primary Examiner*—Patricia L. Morris
(74) *Attorney, Agent, or Firm*—Mark Chao; Elaine M. Ramesh

(57) ABSTRACT

A quaternized nitrogen-containing imidazol-1-yl or 1,2,4-triazol-1-yl compound wherein one of the nitrogen atoms constituting an azole ring is quaternized with a substituent capable of being eliminated in vivo and the substituent can be eliminated in vivo to be converted into an antifungal azole compound, has an improved solubility in water, can advantageously be applied to injection, has an improved internal absorption and can be expected to have a good effect for the treatment or prevention of disease.

5 Claims, 2 Drawing Sheets

AZOLE COMPOUNDS, THEIR PRODUCTION AND THEIR USE

This application is the National stage of International Application No. PCT/JP98/01441, filed on Mar. 30, 1998.

TECNICAL FIELD

The present invention relates to novel azole compounds having an antifungal action, their production and their use.

BACKGROUND ART

Various azole compounds having an antifungal action have hitherto been known. For example, Japanese Patent Kokai Publication No. Hei 6-293740 discloses an azole compound represented by the formula:

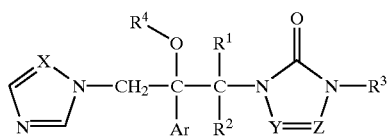

(wherein Ar is a substituted phenyl group; $R^1$ and $R^2$ independently are a hydrogen atom or a lower alkyl group, or $R^1$ and $R^2$ may combine together to form a lower alkylene group; $R^3$ is a group bonded through a carbon atom; $R^4$ is a hydrogen atom or an acyl group; X is a nitrogen atom or a methine group; and Y and Z independently are a nitrogen atom or a methine group which may optionally be substituted with a lower alkyl group) or a salt thereof. Japanese Patent Kokai Publication No. Hei 8-104676 discloses a compound represented by the formula:

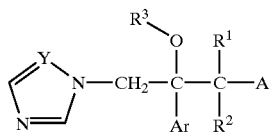

(wherein Ar is an optionally substituted phenyl; $R^1$ and $R^2$ are, the same or different, a hydrogen atom or a lower alkyl group, or $R^1$ and $R^2$ may combine together to form a lower alkylene group; $R^3$ is a hydrogen atom or an acyl group; Y is a nitrogen atom or a methine group; and A is an optionally-substituted saturated cyclic amide group bonded through a first nitrogen atom) and salts thereof. WO 9625410 $A_1$ (corresponding to Japanese Patent Kokai Publication No. Hei 9-183769) discloses a compound represented by the formula:

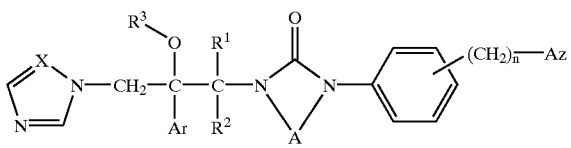

[wherein Ar is an optionally substituted phenyl group; $R^1$ and $R^2$, the same or different, are a hydrogen atom or a lower alkyl group, or $R^1$ and $R^2$ may combine together to form a lower alkylene group; $R^3$ is a hydrogen atom or an acyl group; X is a nitrogen atom or a methine group; A is Y=Z (Y and Z, the same or different, are a nitrogen atom or a methine group optionally substituted with a lower alkyl group) or an ethylene group optionally substituted with a lower alkyl group; n is an integer of 0 to 2; and Az is an optionally substituted azolyl group] or a salt thereof.

On the other hand, a series of compounds referred to as a soft drug have hitherto been known as a quaternary ammonium salt type derivative of an azole (imidazole, triazole) compound which is hydrolyzed enzymatically and/or non-enzymatically. For example, quaternary ammonium salt derivatives of 1-methylimidazole are reported in Journal of Medicinal Chemistry, Vol. 23, page 469, 1980 (antibacterial activity), ibid., Vol. 23, 566, 1980 (antitumor activity), ibid., Vol. 23, 474, 1980 (anticholinergic activity) and ibid., Vol. 32, 493, 1989 (acetylcholine esterase reactivation activity), and these quaternary salts themselves have a biological activity and it is one of their features that hydrolysis thereof occurs rapidly. On the other hand, a quaternary ammonium salt type derivative of azole compounds as a kind of prodrug has been reported only in Pharmaceutical Research Vol. 9, page 372, 1992 (antiglaucoma drug) and Entomologia Experimentalis et Aplicata, Vol. 44, page 295, 1987 (insecticide). In addition, an example of use as a synthetic intermediate of a quaternary ammonium type derivative of imidazole, utilizing its easily hydrolysable property, is reported in Journal of Chemical Society Perkin I, page 1341, 1979 and New Journal of Chemistry, Vol. 16, page 107, 1992. Moreover, a series of quaternary ammonium salt type derivatives are described in U.S. Pat. Nos. 4,061,722 and 4,160,099. However, enzymatically and/or non-enzymatically hydrolyzed quaternary salt derivatives of the azole compounds having an antifungal activity have never been disclosed.

Regarding the azole compounds having the above antifungal activity, the solubility in water for use as an injection preparation is not always sufficient, and it is hard to say that internal absorption is sufficient for demonstrating high therapeutic effect. Therefore, an improvement in solubility in water and in internal absorption have been desired.

DISCLOSURE OF INVENTION

Under these circumstances, the present inventors have studied intensively. As a result, the present inventors have found that a derivative prepared by quaternizing nitrogen atoms contained in a 1H-imidazol-1-yl group or 1H-1,2,4-triazol-1-yl group of azole compounds has an improved solubility in water, and is enzymatically and/or non-enzymatically hydrolyzed to produce a compound which has a 1H-imidazol-1-yl group or 1H-1,2,4-triazol-1-yl group and has an antifungal activity. Thus, the present invention has been accomplished based on this finding.

Namely, the present invention relates to a quaternized nitrogen-containing imidazol-1-yl or 1,2,4-triazol-1-yl compound wherein one of nitrogen atoms constituting an azole ring is quaternized with a substituent capable of being eliminated in vivo and the substituent can be eliminated in vivo to be converted into an antifungal azole compound; a method for producing the same; and a pharmaceutical composition containing the compound.

The above "quaternized nitrogen-containing imidazol-1-yl or 1,2,4-triazol-1-yl compound wherein one of nitrogen atoms constituting an azole ring is quaternized with a substituent capable of being eliminated in vivo and the substituent can be eliminated in vivo to be converted into an antifungal azole compound "[hereinafter referred to as a compound (I),]" is a compound having an imidazol-1-yl or 1,2,4-triazol-1-yl group in the molecule, in which the nitrogen atom is quaternized by having a substituent in the nitrogen atom at the 3-position of the imidazol-1-yl group and the nitrogen atom at the 2- or 4-position of the 1,2,4-triazol-1-yl group, and the substituent is hydrolyzed in vivo to eliminate, thereby being converted into a compound which has an imidazol-1-yl group or 1,2,4-triazol-1-yl group having no quaternized nitrogen atom and has an antifungal action.

Examples of such a compound include a compound represented by the formula:

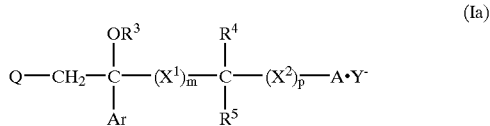

(Ia)

(wherein Q represents an imidazol-1-yl or 1,2,4-triazol-1-yl group in which one of nitrogen atoms constituting an azole ring is quaternized with a substituent capable of being eliminated in vivo; Ar represents an optionally substituted phenyl group; A represents an optionally substituted hydrocarbon or an optionally substituted heterocyclic group; $X^1$ represents an oxygen atom or a methylene group; $X^2$ represents an optionally oxidized sulfur atom; m and p respectively represent 0 or 1; $Y^-$ represents an anion; and ① $R^3$, $R^4$ and $R^5$ may be the same or different and represent a hydrogen atom or a lower alkyl group, or ② $R^3$ represents hydrogen atom or a lower alkyl group, and $R^4$ and $R^5$ are combined with each other to represent a lower alkylene group, or ③ $R^5$ represents a hydrogen atom or a lower alkyl group, and $R^3$ and $R^4$ are combined with each other to represent a lower alkylene group) or a salt thereof [hereinafter referred to as a compound (Ia), sometimes].

"A substituent capable of being eliminated in vivo" in the "imidazol-1-yl or 1,2,4-triazol-1-yl group in which one of nitrogen atoms constituting an azole ring is quaternized with a substituent capable of being eliminated in vivo" represented by Q may be any group which is eliminated in vivo, and the group represented by Q includes those represented by the formula (II):

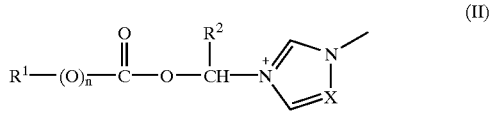

(II)

(wherein $R^1$ represents an optionally substituted hydrocarbon group or heterocyclic group; R 2represents a hydrogen atom or a lower alkyl group; X represents a nitrogen atom or a methine group; and n represents 0 or 1).

Examples of the "hydrocarbon group" of the "optionally substituted hydrocarbon group" represented by $R^1$ includes aliphatic hydrocarbon group, aromatic hydrocarbon group and aromatic-aliphatic hydrocarbon group. Examples of the aliphatic hydrocarbon group include alkyl group, cycloalkyl group, cycloalkylalkyl group, alkenyl group and alkynyl group. Examples of the alkyl group include straight-chain or branched alkyl group having 1 to 20 carbon atoms, such as methyl, ethyl, n-propyl, isopropyl, n-butyl, isobutyl, sec-butyl, tert-butyl, pentyl, hexyl, heptyl, octyl, nonyl, decyl, dodecyl, etc., and among them, lower alkyl group having 1 to 6 carbon atoms (e.g. methyl, ethyl, n-propyl, isopropyl, n-butyl, isobutyl, sec-butyl, tert-butyl, etc.) is particularly preferable. Examples of the cycloalkyl group include cycloalkyl group having 3 to 10 carbon atoms, such as cyclopropyl, cyclobutyl, cyclopentyl, cyclohexyl, cycloheptyl, cyclooctyl, adamantyl, etc., and among them, cycloalkyl group having 3 to 6 carbon atoms (e.g. cyclopropyl, cyclobutyl, cyclopentyl, cyclohexyl, etc.) is particularly preferable. Examples of the cycloalkylalkyl group include those having 4 to 12 carbon atoms, such as cyclopropylmethyl, cyclopentylmethyl, cyclohexylmethyl, etc., and among them, cycloalkylalkyl group having 6 to 8 carbon atoms (e.g. cyclopentylmethyl, cyclohexylmethyl, etc.) is particularly preferable. Examples of the alkenyl group include those having 2 to 4 carbon atoms, such as vinyl, propenyl, butenyl, etc., and among them, alkenyl having 2 to 3 carbon atoms (e.g. vinyl, propenyl) is particularly preferable. Examples of the alkynyl group include those having 2 to 4 carbon atoms, such as ethynyl, propynyl, butynyl, etc., and among them, alkynyl having 2 to 3 carbon atoms (e.g. ethynyl, propynyl) is particularly preferable.

Examples of the aromatic hydrocarbon group include those having 6 to 14 carbon atoms, such as phenyl, naphthyl, biphenylyl, anthryl, indenyl, etc., and among them, aryl group having 6 to 10 carbon atoms (e.g. phenyl, naphthyl, etc.) is particularly preferable.

Examples of the aromatic-aliphatic hydrocarbon group include aralkyl groups having 7 to 15 carbon atoms, such as benzyl, phenethyl, phenylpropyl, naphthylmethyl, indanyl, indanylmethyl, 1,2,3,4-tetrahydronaphthyl, 1,2,3,4-tetrahydronaphthylmethyl, etc., and among them, aralkyl groups having 7 to 11 carbon atoms (e.g. benzyl, phenethyl, naphthyl-methyl, etc.) are particularly preferable.

The "heterocyclic group" of the "optionally substituted heterocyclic group" represented by $R^1$ is a group obtained by removing one of hydrogen atoms linked to a heterocyclic ring, and such a heterocyclic ring represents a 5- to 8-membered ring containing 1 to several, preferably 1 to 4 hetero atoms (e.g. nitrogen atom (optionally oxidized), oxygen atom, sulfur atom, etc.), or a condensed ring thereof. Specific examples of the heterocyclic ring group include pyrrolyl, pyrazolyl, imidazolyl, 1,2,3-triazolyl, 1,2,4-triazolyl, tetrazolyl, furyl, thienyl, oxazolyl, isoxazolyl, 1,2,3-oxadiazolyl, 1,2,4-oxadiazolyl, 1,2,5-oxadiazolyl, 1,3,4-oxadiazolyl, thiazolyl, isothiazolyl, 1,2,3-thiadiazolyl, 1,2,4-thiadiazolyl, 1,2,5-thiadiazolyl, 1,3,4-thiadiazolyl, pyrrolidinyl, pyridyl, pyridazinyl, pyrimidinyl, pyrazinyl, piperidinyl, piperazinyl, indolyl, pyranyl, thiopyranyl, dioxinyl, dioxolyl, quinolyl, pyrido[2,3-d]pyrimidyl, 1,5-, 1,6-, 1,7-, 1,8-, 2,6- or 2,7-naphthyridinyl, thieno[2,3-d]pyridyl, benzopyranyl, tetrahydrofuryl, tetrahydropyranyl, dioxolanyl, dioxanyl and the like.

Examples of the substituent in the "optionally substituted hydrocarbon group" and "optionally substituted heterocyclic group" represented by $R^1$ include heterocyclic group, oxo group, hydroxy group, $C_{1-6}$ alkoxy group, $C_{3-10}$ cycloalkyloxy group, $C_{6-10}$ aryloxy group, $C_{7-19}$ aralkyloxy group, heterocyclic ring-oxy group, mercapto group, $C_{1-6}$ alkylthio group (sulfur atom may be oxidized), $C_{3-10}$ cycloalkylthio group (sulfur atom may be oxidized), $C_{6-10}$ arylthio group (sulfur atom may be oxidized), $C_{7-19}$ aralkylthio group (sulfur atom may be oxidized), a heterocyclic ring-thio group, a heterocyclic ring-sulfinyl group, a heterocyclic ring-sulfonyl group, an amino group, mono-$C_{1-6}$ alkylamino group, di-$C_{1-6}$ alkylamino group, tri-$C_{1-6}$ alkylammonio group, $C_{3-10}$ cycloalkylamino group, $C_{6-10}$ arylamino group, $C_{7-19}$ aralkylamino group, heterocyclic ring-amino group, cyclic amino group, nitro group, halogen atom, cyano group, carboxyl group, $C_{1-10}$ alkoxy-carbonyl group, $C_{6-10}$ aryloxy-carbonyl group, $C_{7-19}$ aralkyloxy-carbonyl group, $C_{6-10}$ aryl-carbonyl group, $C_{1-6}$ alkanoyl group, $C_{3-5}$ alkenoyl group, $C_{6-10}$ aryl-carbonyloxy group, $C_{2-6}$ alkanoyloxy group, $C_{3-5}$ alkenoyloxy group, optionally substituted carbamoyl group, optionally substituted thiocarbamoyl group, optionally substituted carbamoyloxy group, $C_{1-6}$ alkanoylamino group, $C_{6-10}$ aryl-carbonylamino group, $C_{1-10}$ alkoxy-carboxamido group, $C_{6-10}$ aryloxy-carboxamido group, $C_{7-19}$ aralkyloxy-carboxamido group, $C_{1-10}$ alkoxy-carbonyloxy group, $C_{6-10}$ aryloxy-carbonyloxy group, $C_{7-19}$ aralkyloxy-carbonyloxy group, $C_{3-10}$ cycloalkyloxy-carbonyloxy group, optionally substituted ureido group, etc., and they may be the same or different and 1 to 4 substituents may be present. Examples of the "$C_{1-6}$ alkoxy group" include methoxy, ethoxy, n-propoxy, isopropoxy, n-butoxy, tert-butoxy, n-pentyloxy, n-hexyloxy, etc.; "examples of the $C_{3-10}$ cycloalkyloxy group" include cyclopropyloxy, cyclohexyloxy, etc.; examples of the "$C_{6-10}$ aryloxy group" include phenoxy, naphthyloxy, etc.; examples of the "$C_{7-19}$ aralkyloxy group" include benzyloxy, 1-phenylethyloxy, 2-phenylethyloxy, benzhydryloxy, etc.; examples of the "$C_{1-6}$ alkylthio group (sulfur atom may be oxidized)" include methylthio, ethylthio, n-propylthio, n-butylthio, methylsulfinyl, methysulfonyl, etc.; examples of the "$C_{3-10}$ cycloalkylthio group (sulfur atom may be oxidized)" include cyclopropylthio, cyclohexylthio, cyclopentylsulfinyl, cyclohexylsulfonyl, etc.; examples of the "$C_{6-10}$ arylthio group (sulfur atom may be oxidized)" include phenylthio, naphthylthio, phenylsulfinyl, phenylsulfonyl, etc.; examples of the "$C_{7-19}$ aralkylthio group (sulfur atom may be oxidized)" include benzylthio, phenylethylthio, benzhydrylthio, benzylsulfinyl, benzylsulfonyl, etc.; examples of the "mono-$C_{1-6}$ alkylamino group" include methylamino, ethylamino, n-propylamino, n-butylamino, etc.; examples of the "di-$C_{1-6}$ alkylamino group" include dimethylamino, diethylamino, methylethylamino, di-(n-propyl)amino, di-(n-butyl)amino, etc.; examples of the "tri-$C_{1-6}$ alkylammonio groups" include trimethylammonio, etc.; examples of the "$C_{3-10}$ cycloalkylamino group" include cyclopropylamino, cyclopentylamino, cyclohexylamino, etc.; examples of the "$C_{6-10}$ arylamino group" include anilino, N-methylanilino, etc.; examples of the "$C_{7-19}$ aralkylamino group" include benzylamino, 1-phenylethylamino, 2-phenylethylamino, benzhydrylamino, etc.; examples of the "cyclic amino group" include 1-pyrrolidinyl, piperidino, 1-piperazinyl, morpholino, thiomorpholino, etc.; examples of the "halogen atom" include fluorine, chlorine, bromine, iodine, etc.; examples of the "$C_{1-10}$ alkoxy-carbonyl group" include methoxycarbonyl, ethoxycarbonyl, n-propoxycarbonyl, isopropoxycarbonyl, n-butoxycarbonyl, isobutoxycarbonyl, tert-butoxycarbonyl, cyclopentyloxycarbonyl, cyclohexyloxycarbonyl, norbornyloxycarbonyl, etc.; "$C_{6-10}$ aryloxy-carbonyl group" include phenoxycarbonyl, naphthyloxycarbonyl, etc.; examples of the "$C_{7-19}$ aralkyloxy-carbonyl group" include benzyloxycarbonyl, benzhydryloxycarbonyl, etc.; examples of the "$C_{6-10}$ aryl-carbonyl group" include benzoyl, naphthoyl, phenylacetyl, etc.; examples of the "$C_{1-6}$ alkanoyl group" include formyl, acetyl, propionyl, butyryl, valeryl, pivaloyl, etc.; examples of the "$C_{3-5}$ alkenoyl group" include acryloyl, crotonoyl, etc.; examples of the "$C_{6-10}$ aryl-carbonyloxy group" include benzoyloxy, naphthoyloxy, phenylacetoxy, etc.; examples of the "$C_{2-6}$ alkanoyloxy group" include acetoxy, propionyloxy, butyryloxy, valeryloxy, pivaloyloxy, etc.; examples of the "$C_{3-5}$ alkenoyloxy group" include acryloyloxy, crotonoyloxy, etc.; examples of the "optionally substituted carbamoyl group" include carbamoyl group which may be substituted with one or two substituents selected from $C_{1-4}$ alkyl group (e.g. methyl, ethyl, etc.), phenyl group, $C_{1-7}$ acyl group (e.g. acetyl, propionyl, benzoyl, etc.) and $C_{1-4}$ alkoxy-phenyl group (e.g. methoxyphenyl, etc.), and cyclic aminocarbonyl group, and specific examples thereof include carbamoyl, N-methylcarbamoyl, N-ethylcarbamoyl, N,N-dimethylcarbamoyl, N, N-diethylcarbamoyl, N-phenylcarbamoyl, N-acetylcarbamoyl, N-benzoylcarbamoyl, N-(p-methoxyphenyl)carbamoyl, 1-pyrrolidinylcarbonyl, piperidinocarbonyl, 1-piperazinylcarbonyl, morpholinocarbonyl, etc.; examples of the "optionally substituted thiocarbamoyl group" include thiocarbamoyl groups which may be substituted by one or two substituents selected from $C_{1-4}$ alkyl group (e.g. methyl, ethyl, etc.) and phenyl group, and specific examples thereof include thiocarbamoyl, N-methylthiocarbamoyl, N-phenylthiocarbamoyl, etc.; examples of the "optionally substituted carbamoyloxy group" include carbamoyloxy groups which may be substituted with one or two substituents selected from $C_{1-4}$ alkyl group (e.g. methyl, ethyl, etc.) and phenyl group, and specific examples thereof include carbamoyloxy, N-methylcarbamoyloxy, N,N-dimethylcarbamoyloxy, N-ethylcarbamoyloxy, N-phenylcarbamoyloxy, etc.; examples of the "$C_{1-6}$ alkanoylamino group" include acetamido, propionamido, butyramido, valelamido, pivalamido, etc.; examples of the "$C_{6-10}$ aryl-carbonylamino group" benzamido, naphthamido, phthalimido, etc.; examples of the "$C_{1-10}$ alkoxy-carboxamido group" include methoxycarboxamido ($CH_3$ OCONH—), ethoxycarboxamido, tert-butoxycarboxamido, etc.; examples of the "$C_{6-10}$ aryloxy-carboxamido group" include phenoxycarboxamido ($C_6H_5$OCONH—), etc.; examples of the "$C_{7-10}$ aralkyloxy-carboxamido group" include benzyloxycarboxamido ($C_6H_5CH_2$OCONH—), benzhydryloxycarboxamido, etc.; examples of the "$C_{1-10}$alkoxy-carbonyloxy group" include methoxycarbonyloxy, ethoxycarbonyloxy, n-propoxycarbonyloxy, isopropoxycarbonyloxy, n-butoxycarbonyloxy, tert-butoxycarbonyloxy, n-pentyloxycarbonyloxy, n-hexyloxycarbonyloxy, etc.; examples of the "$C_{6-10}$ aryloxy-carbonyloxy group" include phenoxycarbonyloxy, naphthyloxycarbonyloxy, etc.; examples of the "$C_{7-19}$ aralkyloxy-carbonyloxy group" include benzyloxycarbonyloxy, 1-phenylethyloxycarbonyloxy, 2-phenylethyloxycarbonyloxy, benzhydryloxycarbonyloxy, etc.; examples of the "$C_{3-10}$ cycloalkyloxy-carbonyloxy group" include cyclopropyloxycarbonyloxy, cyclohexyloxycarbonyloxy, etc.; and examples of the "optionally substituted ureido group" include ureido group which may be substituted with 1 to 3 substituents selected from $C_{1-4}$ alkyl group (e.g. methyl, ethyl, etc.), phenyl group, etc., and specific examples thereof include ureido, 1-methylureido, 3-methylureido, 3,3-dimethylureido, 1,3-dimethylureido, 3-phenylureido, etc.

As the substituent of the "optionally substituted heterocyclic group" represented by $R^1$, for example, $C_{1-6}$ alkyl group, $C_{3-6}$ cycloalkyl group, $C_{4-7}$ cycloalkylalkyl group, $C_{2-3}$ alkenyl group, $C_{2-3}$ alkynyl group, $C_{6-10}$ aryl group, $C_{7-11}$ aralkyl group, etc. are used, in addition to those described above. Examples of the "$C_{1-6}$ alkyl group" include methyl, ethyl, n-propyl, isopropyl, n-butyl, isobutyl, sec-butyl, tert-butyl, etc.; examples of the "$C_{3-6}$ cycloalkyl group" include cyclopropyl, cyclobutyl, cyclopentyl, cyclohexyl, etc.; examples of the "$C_{4-7}$ cycloalkylalkyl group" include cyclopropylmethyl, cyclopentylmethyl, etc.; examples of the "$C_{2-3}$ alkenyl group" include vinyl, propenyl, etc.; examples of the "$C_{2-3}$ alkynyl group" include ethynyl, propynyl, etc.; examples of the "$C_{6-10}$ aryl group" include phenyl, naphthyl, etc.; and examples of the "$C_{7-11}$ aralkyl group" include benzyl, phenethyl, naphthylmethyl, etc. The number of these substituents of the "optionally substituted hydrocarbon group" and "optionally substituted hetercyclic group".

The heterocyclic group in the substituent of the "hydrocarbon group" and "heterocyclic group", and the heterocyclic group in the heterocyclic ring-oxy group, heterocyclic ring-thio group, heterocyclic ring-sulfinyl group, heterocyclic ring-sulfonyl group and heterocyclic ring-amino group respectively represent a group obtained by removing one of the hydrogen atoms linked to the heterocyclic ring, and such heterocyclic ring represents a 5- to 8-membered ring containing 1 to several, preferably 1 to 4 hetero atoms (e.g. nitrogen atom (optionally oxidized), oxygen atom, sulfur atom, etc.), or a condensed ring thereof. Examples of the heterocyclic group include pyrrolyl, pyrazolyl, imidazolyl, 1,2,3-triazolyl, 1,2,4-triazolyl, tetrazolyl, furyl, thienyl, oxazolyl, isoxazolyl, 1,2,3-oxadiazolyl, 1,2,4-oxadiazolyl, 1,2,5-oxadiazolyl, 1,3,4-oxadiazolyl, thiazolyl, isothiazolyl, 1,2,3-thiadiazolyl, 1,2,4-thiadiazolyl, 1,2,5-thiadiazolyl, 1,3,4-thiadiazolyl, pyrrolidinyl, pyridyl, pyridazinyl, pyrimidinyl, pyrazinyl, piperidinyl, piperazinyl, indolyl, pyranyl, thiopyranyl, dioxinyl, dioxolyl, quinolyl, pyrido[2,3-d]pyrimidyl, 1,5-, 1,6-, 1,7-, 1,8-, 2,6- or 2,7-naphthyridinyl, thieno[2,3-d]pyridyl, benzopyranyl, tetrahydrofuryl, tetrahydropyranyl, dioxolanyl, dioxanyl, etc. These heterocyclic group may be substituted with 1 to 3 substituents selected from $C_{1-4}$ alkyl group (e.g. methyl, ethyl, etc.), hydroxyl group, oxo group and $C_{1-4}$ alkoxy group (e.g. methoxy, ethoxy, etc.).

In the optionally substituted hydrocarbon group or heterocyclic group represented by $R^1$, as the "optionally substituted hydrocarbon group", $C_{1-6}$ alkyl group (examples of the $C_{1-6}$ alkyl group include methyl, ethyl, n-propyl, isopropyl, n-butyl, isobutyl, tert-butyl, etc.) which may be substituted with 1 to 3 substituents selected from hydroxyl, $C_{1-6}$ alkoxy group, $C_{7-19}$ aralkyloxy group, $C_{1-6}$ alkylthio group, $C_{1-6}$ alkylsulfonyl, $C_{1-6}$ alkanoylamino group, $C_{1-10}$ alkoxy-carbonyl group, $C_{7-19}$ aralkyloxy-carbonyl group, optionally substituted carbamoyl group, $C_{1-10}$ alkoxycarboxamido, $C_{7-10}$ aralkyloxy-carboxamido and heterocyclic group (optionally substituted) is preferable, and specific examples thereof include methyl, ethyl, n-propyl, isopropyl, n-butyl, isobutyl, tert-butyl, methoxymethyl, ethoxymethyl, 1-methoxyethyl, 2-methoxyethyl, 1-ethoxyethyl, 2-ethoxyethyl, 2-benzyloxyethyl, 3-benzyloxypropyl, 1,3-dibenzyloxy-2-propyl, hydroxymethyl, 1-hydroxyethyl, 2-hydroxyethyl, 3-hydroxypropyl, 2,3-dihydroxypropyl, 1,3-dihydroxy-2-propyl, methylthiomethyl, methylsulfonylethyl, acetamidomethyl, 1-acetamidoethyl, 2-acetamidoethyl, methoxycarbonylmethyl, ethoxycarbonylmethyl, tert-butoxycarbonylmethyl, 1-ethoxycarbonylethyl, 2-ethoxycarbonylethyl, 1-methoxycarbonyl-1-methylethyl, 1-ethoxycarbonyl-1-methylethyl, 1-tert-butoxycarbonyl-1-methylethyl, 1-benzyloxycarbonylethyl, 1-benzyloxycarbonyl-1-methylethyl, carbamoylmethyl, N,N-dimethylcarbamoylmethyl, methoxycarboxamidomethyl, ethoxycarboxamidomethyl, tert-butoxycarboxamidomethyl, benzyloxycarboxamidomethyl, 2-ethoxycarboxamidoethyl, 2-furylmethyl, 2-tetrahydrofurylmethyl, 1,3-dioxolan-2-ylmethyl, 1,3-dioxolan-4-ylmethyl, 2-oxo-1,3-dioxolan-4-ylmethyl, 2,2-dimethyl-1,3-dioxolan-4-ylmethyl, 1,3-dioxan-5-ylmethyl, 1-ethoxycarbonyl-1-(2,3,4-trihydroxyphenyl)methyl, 1-acetamido-2-ethoxycarbonyl, 1-acetamido-3-ethoxycarbonylpropyl, 2-acetamido-2-ethoxycarbonylethyl, 3-acetamido-3-ethoxycarbonylpropyl, 1-acetamido-2-carbamoylethyl, 1-acetamido-3-carbamoylpropyl, etc.

Among the above $C_{1-6}$ alkyl groups which may be substituted with 1 to 3 substituents, the most preferable ones include straight-chain or branched $C_{1-4}$ alkyl group, such as methyl, ethyl, n-propyl, isopropyl, n-butyl, isobutyl, tert-butyl, etc.; and straight-chain or branched $C_{1-4}$ alkyl group substituted with hydroxyl group, $C_{1-6}$ alkoxy group, $C_{1-10}$ alkoxy-carbonyl group, heterocyclic group (optionally substituted), etc., such as 2-hydroxyethyl, 3-hydroxypropyl, 2,3-dihydroxypropyl, 1,3-dihydroxy-2-propyl, 2-methoxyethyl, 2-ethoxyethyl, 3-benzyloxypropyl, ethoxycarbonylmethyl, 1-ethoxycarbonylethyl, 1-benzyloxycarbonylethyl, 2-furylmethyl, 2-tetrahydrofurylmethyl, 1,3-dioxolan-4-ylmethyl, 2-oxo-1,3-dioxolan-4-ylmethyl, 2,2-dimethyl-1,3-dioxolan-4-ylmethyl, etc.

In the optionally substituted hydrocarbon group or heterocyclic group represented by $R^1$, as the "optionally substituted heterocyclic group", a heterocyclic group substituted with 1 to 3 substituents selected from oxo group, hydroxyl group, $C_{1-6}$ alkyl group, $C_{1-6}$ alkoxy group, etc. are preferable, and specific examples thereof include furyl, thienyl, pyranyl, thiopyranyl, dioxinyl, dioxolyl, benzopyranyl, tetrahydrofuryl, tetrahydropyranyl, dioxolanyl, dioxanyl, methylfuryl, hydroxyfuryl, methylthienyl, methoxyfuryl, 2-oxo-1,3-dioxolyl, 2,2-dimethyl-1,3-dioxolyl, 2-oxo-1,3-dioxolanyl, 2,2-dimethyl-1,3-dioxolanyl, 2-oxo-1,3-dioxanyl, 2,2-dimethyl-1,3-dioxanyl, etc. Among them, furyl, thienyl, dioxanyl, 2-oxo-1,3-dioxanyl, 2,2-dimethyl-1,3-dioxanyl are particularly preferable.

Examples of the lower alkyl group represented by $R^2$ include lower alkyl group having 1 to 4 carbon atoms (e.g. methyl, ethyl, propyl, isopropyl, butyl, isobutyl, sec-butyl, tert-butyl, etc.), and methyl is particularly preferable.

As $R^2$, a hydrogen atom or methyl is particularly preferable.

X represents a nitrogen atom or a methine group, and a nitrogen atom is preferable.

Examples of the optionally oxidized sulfur atom represented by $X^2$ includes thio, sulfinyl and sulfonyl.

m and p respectively represent an integer of 0 or 1, and the care where both of them are 0 is preferable.

Examples of the substituent in the "optionally substituted phenyl group" represented by Ar include halogen (e.g. fluorine, chlorine, bromine, iodine, etc.), halogenated lower ($C_{1-4}$) alkyl group (e.g. fluoromethyl, trifluoromethyl, chloromethyl, 1-fluoroethyl, 2-fluoroethyl, 1,1-difluoroethyl, 1,2-difluoroethyl, etc.) and halogenated lower ($C_{1-4}$) alkoxy group (e.g. fluoromethoxy, trifluoromethoxy, chloromethoxy, 1-fluoroethoxy, 2-fluoroethoxy, 1,1-difluoroethoxy, 1,2-difluoroethoxy, 1,1,2,2-tetrafluoroethoxy, 2,2,2-trifluoroethoxy, 2,2,3,3-tetrafluoropropoxy, 2,2,3,3,3-pentafluoropropoxy, etc.). The substituent is preferably a halogen (e.g. fluorine, chlorine, bromine, iodine, etc.), more preferably fluorine. The number of substituents is preferably 1 to 3, more preferably 1 to 2.

Preferred examples of Ar include halogenophenyl group, halogenated lower ($C_{1-4}$) alkylphenyl group, halogenated lower ($C_{1-4}$) alkoxyphenyl group, etc. Examples of the halogenophenyl group include 2,4-difluorophenyl, 2,4-dichlorophenyl, 4-chlorophenyl, 4-fluorophenyl, 2-chlorophenyl, 2-fluorophenyl, 2-fluoro-4-chlorophenyl, 2-chloro-4-fluorophenyl, 2,4,6-trifluorophenyl, 4-bromophenyl, etc. Examples of the halogenated lower ($C_{1-4}$) alkylphenyl group include 4-trifluoromethylphenyl, etc. Examples of the halogenated lower ($C_{1-4}$) alkoxyphenyl group include 4-trifluoromethoxyphenyl, 4-(1,1,2,2- tetrafluoroethoxy)phenyl, 4-(2,2,2-trifluoroethoxy)phenyl, 4-(2,2,3,3-tetrafluoropropoxy)phenyl, 4-(2,2,3,3,3-pentafluoropropoxy)phenyl, etc.

Specifically preferable examples of Ar is a phenyl group substituted with 1 to 2 halogens, such as 2,4-difluorophenyl, 2,4-dichlorophenyl, 4-chlorophenyl, 4-fluorophenyl, 2-chlorophenyl, 2-fluorophenyl, 2-fluoro-4-chlorophenyl, 2-chloro-4-fluorophenyl, 4-bromophenyl, etc. Among them, a phenyl group substituted with 1 to 2 fluorine atoms, such as 4-fluorophenyl, 2-fluorophenyl, 2,4-difluorophenyl, etc. is particularly preferable, and 2-fluorophenyl and 2,4-difluorophenyl are more preferable.

An anion represented by $Y^-$ is that obtained by removing one proton from an organic acid or an inorganic acid, and examples of the organic acid include acetic acid, propionic acid, methanesulfonic acid, benzenesulfonic acid, toluenesulfonic acid, trifluoromethanesulfonic acid, trifluoroacetic acid, etc., and examples of the inorganic acid include hydrochloric acid, sulfuric acid, phosphoric acid, hydrofluoric acid, hydrobromic acid, hydroiodic acid, water, etc. As $Y^-$, an anion obtained by removing one proton from an inorganic acid is preferable. Among them, an anion obtained by removing one proton from a hydro-halogenoic acid such as hydrochloric acid, hydrofluoric acid, hydrobromic acid, hydroiodic acid, etc. is preferable, and an anion obtained by removing one proton from hydrochloric acid, hydrobromic acid, hydroiodic acid, etc. is particularly preferable. $Y^-$ can be defined as a group having a negative charge, and preferred examples thereof include $Cl^-$, $F^-$, $Br^-$, $I^-$, $HSO_3^-$, $HSO_4^-$, $H_2PO_4^-$, $OH^-$, etc. Among them, $Cl^-$, $F^-$, $Br^-$, $I^-$ are preferable, and $Cl^-$, $Br^-$ and $I^-$ are particularly preferable.

Examples of the lower alkyl group represented by $R^3$, $R^4$ and $R^5$ include straight-chain or branched alkyl group having 1 to 4 carbon atoms, such as methyl, ethyl, propyl, isopropyl, butyl, isobutyl, sec-butyl, tert-butyl, etc. Among them, methyl is particularly preferable.

When $R^3$ and $R^4$, or $R^4$ and $R^5$ are combined to form a lower alkylene group, examples of the lower alkylene group include those having 1 to 4 carbon atoms, such as methylene, ethylene, propylene, butylene, etc. When $R^3$ and $R^4$ are combined to form a lower alkylene group, methylene and ethylene are preferable. When $R^4$ and $R^5$ are combined to form a lower alkylene group, ethylene is preferable.

$R^3$ is preferably a hydrogen atom. Preferably, $R^4$ and $R^5$ are simultaneously hydrogen atoms or methyl groups, or one of them is a hydrogen atom and the other one is a methyl group. More preferably, one of $R^4$ and $R^5$ is a hydrogen atom and the other one is methyl.

Examples of the "optionally substituted hydrocarbon group" or "optionally substituted heterocyclic group" represented by A includes the same one as that described for $R^1$. A is preferably a group of the formula:

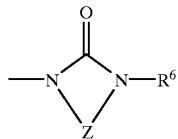

(wherein $R^6$ represents an optionally substituted hydrocarbon group or aromatic heterocyclic group; and Z represents an optionally substituted lower alkylene group or a group of the formula:

—D=E—

(D and E may be same or different and represent a nitrogen atom or a methine group which may be substituted with a lower alkyl)). Examples of the hydrocarbon group in the "optionally substituted hydrocarbon group" represented by $R^6$ include aliphatic hydrocarbon group, aromatic hydrocarbon group and aromatic-aliphatic hydrocarbon group.

Examples of the aliphatic hydrocarbon group include alkyl, cycloalkyl, alkenyl, alkynyl group, etc. Examples of the alkyl groups include straight-chain or branched one having 1 to 12 carbon atoms. Specific examples thereof include methyl, ethyl, n-propyl, isopropyl, n-butyl, isobutyl, sec-butyl, tert-butyl, heptyl, octyl, nonyl, decyl, dodecyl, etc. Among them, a lower alkyl group having 1 to 4 carbon atoms (e.g. methyl, ethyl, n-propyl, isopropyl, n-butyl, isobutyl, sec-butyl, tert-butyl, etc.) is particularly preferable. Examples of the cycloalkyl groups include cycloalkyl groups having 3 to 8 carbon atoms. Specific examples thereof include cyclopropyl, cyclobutyl, cyclopentyl, cyclohexyl, cycloheptyl, cyclooctyl, etc. Among them, a cycloalkyl group having 3 to 6 carbon atoms (e.g. cyclopropyl, cyclobutyl, cyclopentyl, cyclohexyl, etc.) is particularly preferable. Examples of the alkenyl group include alkenyl group having 2 to 4 carbon atoms. Specific examples thereof include vinyl, propenyl, butenyl, etc. Among them, an alkenyl group having 2 to 3 carbon atoms (e.g. vinyl, propenyl, etc.) is particularly preferable. Examples of the alkynyl group include alkynyl group having 2 to 4 carbon atoms. Specific examples thereof include ethynyl, propynyl, butynyl, etc. Among them, an alkynyl group having 2 to 3 carbon atoms (e.g. ethynyl, propynyl, etc.) is particularly preferable.

Examples of the aromatic hydrocarbon group include aryl group having 6 to 14 carbon atoms. Examples of the aryl group include phenyl, naphthyl, biphenylyl, anthryl, indenyl, etc. Among them, an aryl group having 6 to 10 carbon atoms (e.g. phenyl, naphthyl, etc.) is particularly preferable.

Examples of the aromatic-aliphatic hydrocarbon group include arylalkyl groups having 7 to 15 carbon atoms. Specific examples thereof include benzyl, phenethyl, phenylpropyl, naphthylmethyl, indanyl, indanylmethyl, 1,2, 3,4-tetrahydronaphthyl, 1,2,3,4-tetrahydronaphthylmethyl, biphenylmethyl, benzhydryl, etc. Among them, an aralkyl group having 7 to 11 carbon atoms (e.g. benzyl, phenethyl, naphthylmethyl, etc.) is particularly preferable.

Examples of the aromatic heterocyclic group in the "aromatic heterocyclic group which may have a substituent" represented by $R^6$ include aromatic heterocyclic group containing at least one hetero atom selected from nitrogen atom, sulfur atom and oxygen atom. The aromatic heterocyclic group may be condensed with a benzene ring, or 5- or 6-membered heterocyclic ring. Examples of the aromatic heterocyclic group include aromatic heterocyclic group such as imidazolyl, triazolyl, tetrazolyl, pyrazolyl, pyridyl, thiazolyl, thiadiazolyl, thienyl, furyl, pyrrolyl, pyrazinyl, pyrimidinyl, oxazolyl, isooxazolyl, etc.; and condensed aromatic heterocyclic group such as benzimidazolyl, imidazopyrimidinyl, imidazopyridinyl, imidazopyrazinyl, imidazopyridazinyl, benzothiazolyl, quinolyl, isoquinolyl, quinazolinyl, indolyl, etc. As the aromatic heterocyclic group, a 5- or 6-membered aromatic heterocyclic group containing 1 to 3 hetero atoms selected optionally from nitrogen atom, sulfur atom and oxygen atom (e.g. imidazolyl, triazolyl, thiazolyl, thiadiazolyl, thienyl, furyl, pyridyl, pyrimidinyl, etc.) is particularly preferable.

Examples of the substituent in the "aliphatic, aromatic or aromatic-aliphatic hydrocarbon group which may have a substituent, or aromatic heterocyclic group which may have a substituent" represented by $R^6$ include hydroxyl group, optionally esterified carboxyl group (e.g. carboxyl, alkoxycarbonyl having 1 to 6 carbon atoms, such as methoxycarbonyl, ethoxycarbonyl, butoxycarbonyl, etc.), nitro group, amino group, acylamino group (e.g. alkanoylamino having 1 to 10 carbon atoms, such as acetylamino, propionylamino, butyrylamino, etc.), amino group which is mono- or di-substituted with an alkyl group having 1 to 10 carbon atoms (e.g. methylamino, dimethylamino, diethylamino, dibutylamino, etc.), optionally substituted 5- to 6-membered cyclic amino group (e.g. pyrrolidinyl, morpholino, piperidino, pyrazolidinyl, perhydroazepinyl, piperazinyl, 4-benzylpiperazinyl, 4-acetylpiperazinyl, 4-(4-trifluoromethoxyphenyl)-1-piperazinyl, 4-[4-(1,1,2,2-tetrafluoroethoxy)phenyl]-1-piperazinyl, 4-[4-(2,2,3,3-tetrafluoropropoxy)phenyl]-1-piperazinyl, 4-[4-(2,2,2-trifluoroethoxy)phenyl]-1-piperazinyl, 4-[4-(2,2,3,3,3-pentafluoropropoxy)phenyl]-1-piperazinyl, 4-(4-trifluoromethylphenyl)-4-piperazinyl, etc.), alkoxy group having 1 to 6 carbon atoms (e.g. methoxy, ethoxy, propoxy, butoxy, etc.), halogen atom (e.g. fluorine, chlorine, bromine, etc.), alkyl group having 1 to 6 carbon atoms (e.g. methyl, propyl, butyl, etc.), cycloalkyl group having 3 to 6 carbon atoms (e.g. cyclopropyl, cyclopentyl, etc.), halogeno-alkyl group having 1 to 6 carbon atoms (e.g. trifluoromethyl, dichloromethyl, trifluoroethyl, etc.), halogeno-alkoxy group having 1 to 6 carbon atoms (e.g. trifluoromethoxy, 1,1,2,2-tetrafluoroethoxy, 2,2,2-trifluoroethoxy, 2,2,3,3-tetrafluoropropoxy, 2,2,3,3,3-pentafluoropropoxy, 2,2,3,3,4,4,5,5,5-octafluoropentoxy, 2-fluoroethoxy, etc.), oxo group, thioxo group, mercapto group, alkylthio group having 1 to 6 carbon atoms (e.g. methylthio, ethylthio, butylthio, etc.), alkylsulfonyl group having 1 to 6 carbon atoms (e.g. methanesulfonyl, ethanesulfonyl, butanesulfonyl, etc.), alkanoyl group having 1 to 10 carbon atoms (e.g. acetyl, formyl, propionyl, butyryl, etc.), 5- or 6-membered aromatic heterocyclic group (e.g. pyrrolyl, pyrazolyl, imidazolyl, 1,2,3-triazolyl, 1,2,4-triazolyl, tetrazolyl, thiazolyl, isothiazolyl, oxazolyl, isoxazolyl, furazanyl, 1,3,4-thiadiazolyl, 1,2,3-thiadiazolyl, 1,2,5-thiadiazolyl, 1,2,4-thiadiazolyl, thienyl, furyl, pyridyl, pyrimidinyl, pyridazinyl, etc.) and condensed aromatic heterocyclic group (e.g. benzimidazolyl, imidazopyrimidinyl, imidazopyridinyl, imidazopyrazinyl, imidazopyridazinyl, benzothiazolyl, quinolyl, isoquinolyl, quinazolyl, indolyl, etc.). Among them, a halogeno-alkoxy group having 1 to 6 carbon atoms and 5-membered aromatic heterocyclic group is preferable, and 1,1,2,2-tetrafluoroethoxy, 2,2,3,3-tetrafluoropropoxy, pyrazolyl (e.g. 1H-pyrazol-1-yl), imidazolyl (e.g. 1H-imidazol-1-ly), 1,2,3-triazolyl (e.g. 1H-1,2,3-triazol-1-yl, 2H-1,2,3-triazol-2-yl), 1,2,4-triazolyl (e.g. 1H-1,2,4-triazol-1-yl), tetrazolyl (e.g. 1H-tetrazol-1-yl, 2H-tetrazol-2-yl) are particularly preferable.

The number of the above substituents is preferably 1 to 3, more preferably 1 to 2.

The aliphatic, aromatic or aromatic-aliphatic hydrocarbon groups which may have a substituent, or aromatic heterocyclic group which may have a substituent, which is represented by $R^6$, is preferably an aromatic hydrocarbon group which may have a substituent, more preferably a phenyl group having a substituent. Among them, a phenyl group substituted with a halogeno-alkoxy group having 1 to 6 carbon atoms (e.g. 4-(1,1,2,2-tetrafluoroethoxy)phenyl, 4-(2,2,3,3-tetrafluoropropoxy)phenyl) and a phenyl group substituted with a 5-membered aromatic heterocyclic group [e.g. 4-(1H-pyrazol-1-yl)phenyl, 4-(1H-imidazol-1-yl)phenyl, 4-(1H-1,2,3-triazol-1-yl)phenyl, 4-(2H-1,2,3-triazol-2-yl)phenyl, 4-(1H-1,2,4-triazol-1-yl)phenyl, 4-(1H-tetrazol-1-yl)phenyl, 4-(2H-tetrazol-2-yl)phenyl] are particularly preferable.

The lower alkylene group in the "optionally substituted lower alkylene group" represented by Z include those having 1 to 3 carbon atoms, such as methylene, ethylene, propylene, etc. Among them, ethylene is particularly preferable. The substituent in the "optionally substituted lower alkylene group" is preferably a straight-chain or branched alkyl group having 1 to 4 carbon atoms, such as methyl, ethyl, n-propyl, isopropyl, n-butyl, isobutyl, sec-butyl, tert-butyl, etc. Among them, methyl and ethyl are more preferable, and methyl is particularly preferable.

Preferred examples of the ethylene group which may be substituted with a lower alkyl group, which is represented by Z, include ethylene, 1-methylethylene, 1,1-dimethylethylene, 1,2-dimethylethylene, 1-ethylethylene, 1,2-diethylethylene, etc. Among them, ethylene is particularly preferable.

When Z is D=E, examples of lower alkyl group in the "methine group which may be substituted with a lower alkyl group" represented by D or E include straight-chain or branched alkyl group having 1 to 4 carbon atoms (e.g. methyl, ethyl, n-propyl, isopropyl, n-butyl, isobutyl, sec-butyl, tert-butyl, etc.). Among them, methyl is preferable.

Preferred examples of the methine group which may be substituted with a lower alkyl group, represented by D or E, include methine, ethylidyne (—C(CH$_3$)=), propylidyne (—C(CH$_2$CH$_3$)=), butylidyne (—C(CH$_2$CH$_2$CH$_3$)=), etc. Among them, methine and ethylidyne are preferable, and methine is particularly preferable.

The case where one of D and E is a nitrogen atom and the other is methine; the case where both of D and E are methines; the case where both of D and E are nitrogen atoms; and the case where one of D and E is a nitrogen atom and the other is ethylidyne are preferable. Among them, the case where one of D and E is a nitrogen atom and the other one is methine; and the case where both of D and E are methines are particularly preferable.

Specifically, Z is preferably —N=CH—, —CH=N—, —CH=CH—, —N=N—, —N=C(CH$_3$)—, —C(CH$_3$)=N—, —CH$_2$—CH$_2$—, etc. Among them, —N=CH—, —CH=N—, —CH=CH—, —CH$_2$—CH$_2$—, etc. are more preferable, and —N=CH—, —CH$_2$—CH$_2$— are the most preferable.

As the group represented by the formula:

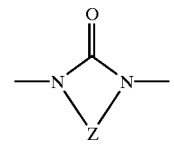

for example,

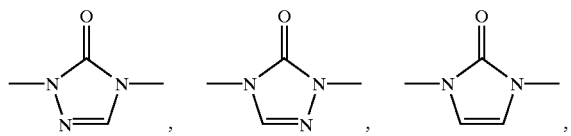

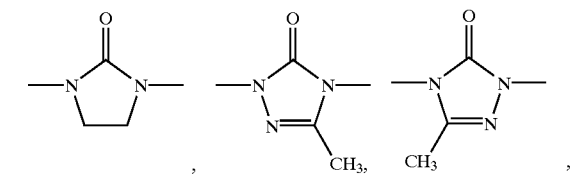

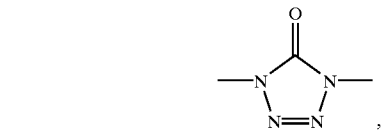

etc. are preferable. Among them,

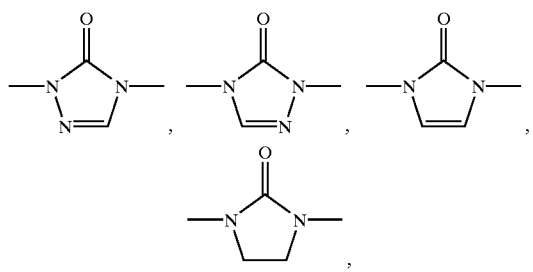

ect. are particularly preferable.

Also, when a reactive atom such as nitrogen atom is present in the optionally substituted hydrocarbon group or optionally substituted heterocyclic group represented by A, a group of formula:

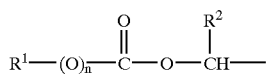

(wherein each symbol is as defined above) may be linked to the atom.

When the compound (I) has one or more asymmetric carbon atoms in the molecule, two or more stereoisomers exist, and the stereoisomers and a mixture thereof are also involved in the present invention. In the compound represented by the general formula (1a), when Q is a group represented by the formula (II), A is

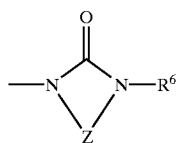

m and p are both 0, $R^4$ is a hydrogen atom and $R^5$ is a methyl group, an optically active compound in which both carbon to which the optionally substituted phenyl group represented by Ar is linked and carbon to which $R^5$ is linked are in the (R) configuration, is particularly preferable.

In the formula (Ia), when Q is a group represented by the formula (II), the formula (Ia) can also be represented by the formula:

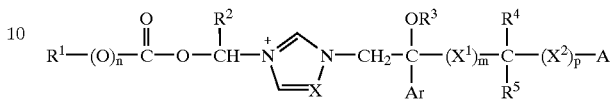

(Ia-1)

or

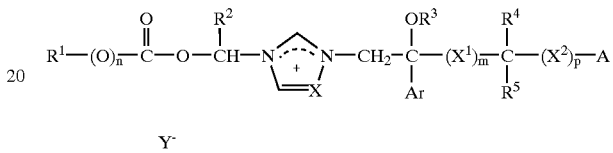

(Ia-2)

(wherein each symbol is as defined above).

The compounds of the present invention can be either a hydrate or a nonhydrate. The compounds of the present invention are converted in vivo into compounds having an antifungal activity, represented by the formula:

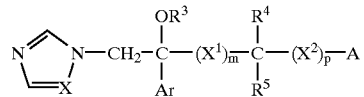

(III)

(wherein each symbol is as defined above).

Specific examples of the compounds according to the present invention are shown in Tables 1 to 4, but are not limited to the exemplified compounds.

TABLE 1

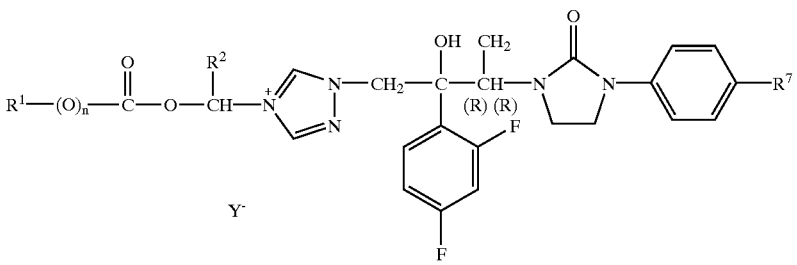

| Compound No. | $R^1$ | n | $R^2$ | Y | $R^7$ |
|---|---|---|---|---|---|
| 1 | $(CH_3)_3C$ | 0 | H | Cl | (triazole) |
| 2 | $(CH_3)_3C$ | 0 | H | Cl | (tetrazole) |

TABLE 1-continued
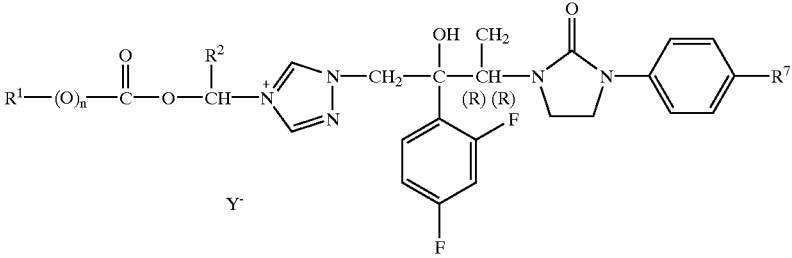
| Compound No. | R¹ | n | R² | Y | R⁷ |
|---|---|---|---|---|---|
| 3 | CH₃ | 0 | H | Cl | 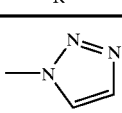 |
| 4 | (CH₃)₂CH | 0 | H | Cl | 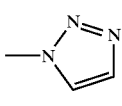 |
| 5 | (CH₃)₂CH | 0 | H | Cl | 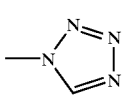 |
| 6 | CH₃CH₂ | 1 | CH₃ | Cl | 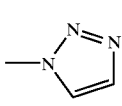 |
| 7 | CH₃CH₂ | 1 | CH₃ | Cl | 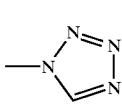 |
| 8 | (CH₃)₃C | 0 | H | Cl | 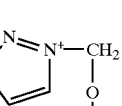 |
| 9 | (CH₃)₂CH | 1 | H | Cl | 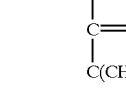 |
TABLE 2
| Compound No. | R¹ | n | R² | Y | R⁷ |
|---|---|---|---|---|---|
| 10 | CH₃ | 0 | H | Br | 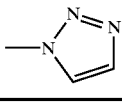 |
| 11 | CH₃ | 0 | H | Br |  |
| 12 | CH₃ | 0 | H | Cl | 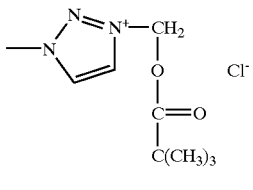 |
| 13 | CH₃CH₂ | 0 | H | Cl | 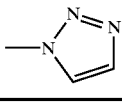 |
| 14 | CH₃CH₂ | 0 | H | Cl | 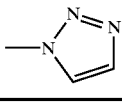 |

TABLE 2-continued
| Compound No. | R¹ | n | R² | Y | R⁷ |
|---|---|---|---|---|---|
| 15 | CH₃CH₂ | 1 | H | Cl |  |
| 16 | CH₃CH₂ | 1 | H | Cl |  |
| 17 | CH₃CH₂ | 1 | H | I |  |
| 18 | (CH₃)₂CH | 1 | H | Cl |  |
| 19 | CH₃CH₂CH₂ | 1 | H | Cl |  |
| 20 | CH₃CH₂CH₂ | 1 | H | I |  |
| 21 |  | 1 | H | Cl |  |
TABLE 3
| Compound No. | R¹ | n | R² | Y | R⁷ |
|---|---|---|---|---|---|
| 22 | 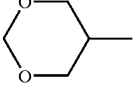 | 1 | H | Cl |  |
| 23 | 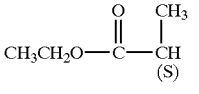 | 1 | H | Cl |  |
| 24 | 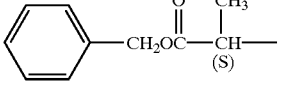 | 1 | H | Cl |  |
| 25 | 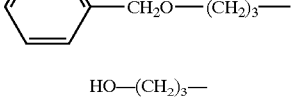 | 1 | H | Cl |  |
| 26 | HO—(CH₂)₃— | 1 | H | Cl |  |
| 27 | 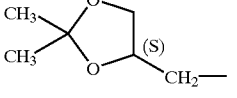 | 1 | H | Cl |  |
| 28 | 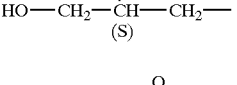 | 1 | H | Cl |  |
| 29 | 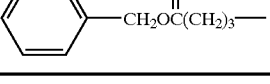 | 1 | H | Cl |  |

TABLE 4

| Compound No. | R¹ | n | R² | Y | R⁷ |
|---|---|---|---|---|---|
| 30 | (tetrahydrofuran-2-yl)CH₂— | 1 | H | I | tetrazol-1-yl |
| 31 | (1,3-dioxan-5-yl)— | 1 | H | I | tetrazol-1-yl |
| 32 | PhCH₂OC(O)(CH₂)₃— | 1 | H | I | tetrazol-1-yl |
| 33 | HOC(O)(CH₂)₃— | 1 | H | Cl | tetrazol-1-yl |
| 34 | CH₃C(O)NH(CH₂)₂— | 1 | H | Cl | tetrazol-1-yl |
| 35 | CH₃O(CH₂)₃— | 1 | H | Cl | tetrazol-1-yl |
| 36 | CH₃—C(O)—O—CH₂—N⁺(triazolyl)—CH₂—C(OH)(2,4-difluorophenyl)(R)—CH(CH₃)(R)—N(triazolinonyl)—C₆H₄—OCH₂CF₂CF₂H, Cl⁻ | | | | |

The compounds of the present invention can be produced by introducing a group, which is capable of being eliminated in vivo, into an antifungal compound having an imidazol-1-yl group or 1,2,4-triazol-1-yl group.

Examples of the antifungal compound having an imidazol-1-yl group or 1,2,4-triazol-1-yl group include known azole antifungal compounds such as miconazole, ketoconazole, fluconazole, itraconazole, saperconazole, clotrimazole, D0870, voriconazole, econazole, isoconazole, sulconazole, butoconazole, tioconazole, bifonazole, croconazole, oxiconazole, terconazole, SSY-726, KP-103, Sch-56592, Sch-51048, UR-9746, MFB-1041, UR-9751, UR-9728, UR-9825, ER-30346, T-8581, BAY-W-9279, fenticonazole, omoconazole, flutrimazole, eberconazole, lanoconazole, neticonazole, sertaconazole, genaconazole, etc., but are not limited to known antifungal agents.

The compound (Ia-1) [the compound (Ia) wherein Q is a group represented by the formula (II)], can be produced, for example, by reacting a compound (III) with a compound represented by the formula (IV):

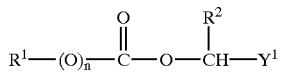
(IV)

(wherein Y¹ represents a halogen atom and other symbols are as defined above)[hereinafter referred to as a compound (IV), sometimes] and optionally subjecting the reaction product to anion exchange.

The halogen atom represented by Y¹ is preferably chlorine, bromine or iodine.

The reaction between the compound (III) and compound (IV) is usually carried out with or without a solvent which does not inhibit the reaction. As the solvent which does not inhibit the reaction, for example, ketones (e.g. acetone, 2-butanone, 2-pentanone, etc.), sulfoxides (e.g. dimethylsulfoxide, etc.), ethers (e.g. diethyl ether, tetrahydrofuran, dioxane, etc.), nitrites, (e.g. acetonitrile, etc.), aromatic hydrocarbons (e.g. benzene, toluene, xylene, etc.), halogenated hydrocarbons, (e.g. dichloromethane, chloroform, 1,2-dichloroethane, etc.), esters (e.g. ethyl acetate, etc.), amides (e.g. dimethylformamide, acetamide, dimethylacetamide, 1-methyl-2-pyrrolidinone, etc.) and ureylenes (e.g. 1,3-dimethyl-2-imidazolidinone, etc.) are used. These solvents can be used alone or in combination thereof in an appropriate ratio.

The compound (IV) is used in an amount of about 1 to 100 equivalent, preferably about 1 to 5 equivalent, based on the compound (III).

The reaction temperature is not specifically limited, but is usually from about 0 to 150° C., preferably from about 20 to 120° C.

The reaction time is from several minutes to several hundred hours (e.g. 5 minutes to 100 hours, etc.).

The compound thus obtained can be optionally converted into a compound (Ia) having a desired anion (Y⁻) by anion exchange. The anion exchange can be carried out by treating with an anion type ion exchange resin, or an alkali metal (e.g. sodium, potassium, etc.) salt of an organic or inorganic acid described above for Y⁻, in the presence of water, a mixed solvent of water and an organic solvent (e.g. acetone, acetonitorile, tetrahydrofuran, methanol, ethanol, etc.) or organic solvent.

The compound (I) of the present invention (hereinafter referred to as a present compound (I), sometimes) thus obtained can be isolated and purified from the reaction mixture using a per se known means such as extraction, concentration, neutralization, filtration, recrystallization, column chromatography, thin layer chromatography, etc.

When the present compound (I) has one or more asymmetric carbon atoms in the molecule, two or more stereoisomers exist, but those isomers can be separately prepared, if desired. For example, when the starting compounds (III) and (IV) have an asymmetric carbon atom in the molecule, a single isomer of the present compound (Ia) can be obtained by carrying out above reaction using such single isomer. In addition, a single isomer of the reaction compound (Ia) can be obtained by carrying out above reaction using a single isomer of the starting compound (III). Also, when the product is a mixture of two or more kinds of isomers, the product can be separated by using a normal separation method, e.g. separation means such as various chromatographies and fractional recrystallization.

When the starting compound (III) of the present invention is a per se known antifungal agent described above, the production method is known and methods of series of compounds which are useful as an antifungal agent are per se known, for example, the methods described in Japanese Patent Kokai Publication No. Hei 6-293740, Japanese Patent Kokai Publication No. Hei 8-104676 and WO-9625410A. In addition, the production method of the other starting compound (IV) is also known, and the compound can be produced by the method described in Synthesis, page 588 (1971) and Synthetic Communications, Vol. 25, page 2739 (1995), or a manner based on the method.

Since the present compound (I) has low toxicity and strong antifungal activity to the *genus Candida* [e.g. *Candida albicans, Candida utilis, Candida glabrata,* etc.], genus Histoplasma [e.g. *Histoplasma capsulatum,* etc.], genus Aspergillus [e.g. *Aspergillus niger, Aspergillus fumigatus,* etc.], genus Cryptococcus [e.g. *Cryptococcus neoformans,* etc.], genus Trichophyton [e.g. *Trichophyton rubrum, Trichophton mentagrophytes,* etc.], genus Microsporum [e.g. *Microsporum gypseum,* etc.], genus Mallassezia [e.g. *Mallassezia furfur,* etc.], etc., it can be used for prevention or treatment of fungal infections [e.g. mucosal candidiasis (oral thrush, angular stomatitis, vulvovaginal candidiasis, candida balanoposthitis and urethritis), dermal candidiasis (interdigital candidiasis, intertriginous candidiasis, perianal candidiasis, blastomycosis cutis eczematosa, candida onychia, candida paronychia, auricular candidiasis, cutaneous lesion of candida septicaemia, diffuse superficial candidiasis, candida granuloma, congenital cutaneous candidiasis, candidids), chronic mucocutaneous candidiasis and systemic candidiasis (candidiasis of the respiratory tract, candidiasis of the gastrointestinal tract,candida septicaemia, candida endocarditis, candidiasis of the urinary tract, candidiasis of the eye, candidiasis of the central nervous system, articular and bone candidiasis, candida peritonitis, candidiasis of the liver, intrauterine candidiasis, etc.) due to genus Candida; acute pulmonary histoplasmosis, chronic pulmonary histoplasmosis and disseminated histoplasmosis, etc. due to genus Histoplasma; aspergillosis of the respiratory tract (allergic aspergillosis, bronchial aspergillosis, aspergilloma, pulmonary aspergillosis (acute invasive pulmonary aspergillosis, chronic necrotizing pulmonary aspergillosis), aspergillary empyema), disseminated aspergillosis, central nervous system aspergillosis, aspergillary endocarditis, aspergillary myocarditis, aspergillary pericarditis, aspergillary mycetoma, aspergillary otomycosis, aspergillary onychia, aspergillary paronychia, aspergillary keratitis, aspergillary endophthalmitis, cutaneous aspergillosis and nasal-orbital aspergillosis, etc. due to genus Aspergillus; pulmonary cryptococcosis, central nervous system cryptococcosis, cutaneous and mucocutaneous cryptococcosis, osseous cryptococcosis, cryptococcosis of lymphnodes, disseminated cryptococcosis and cryptococcosis of hematopoetic organs, etc. due to genus Cryptococcus; tinea capitis, favus, kerion celsi, tinea barbae, trichophytia maculovesiculosa, trichophytia eczematosa marginata, tinea imbricata, trichophytia pompholyciformis, tinea unguium, trichophitid and granuloma trychophyticum, etc. due to genus Trichophyton or genus Microsporum; tinea versicolor, etc. due to genus Mallassezia] in the mammals (e.g. human, domestic animal, fowl, etc.), and can also be used for prevention or treatment of atopic dermatitis. Moreover, the compound (I) of the present invention can be used as an agricultural antifungal agent.

When the present compound (I) is administered to humans, it can be administered orally or parenterally in safety as a pharmaceutical composition such as oral administration (e.g. powder, granule, tablet, capsule, etc.), parenteral administration [e.g. injection, external agent (e.g. nasal administration, percutaneous administration, etc.) and suppository (e.g. rectal suppository, vaginal suppository, etc.)] alone or in combination with appropriate pharmaceutically acceptable carriers, excipients, diluents, etc.

These preparations can be prepared by a per se known method which is usually used in the production process. The proportion of the present compound (I) in the preparation varies depending on the form thereof, and can be in the range usually employed in the antifungal agent. For example, it is about 10 to 95% by weight in case of the above oral administration and is about 0.001 to 95% by weight in case of the above parenteral administration.

For example, the injection can be prepared by mixing the present compound (I) with dispersants [e.g. Tween 80 (manufactured by Atlas Powder company, U.S.A.), HCO 60 (manufactured by Nikko Chemicals Co.), carboxymethylcellose, sodium alginate, etc.], preservatives (e.g. methylparaben, propylparaben, benzyl alcohol, chlorobutanol, etc.) and isotonic agents (e.g. sodium chloride, glycerin, sorbitol, glucose, etc.) to form an aqueous injection, or by dissolving, suspending or emulsifying into vegetable oils (e.g. olive oil, sesame oil, peanut oil, cotton seed oil, corn oil, etc.), propyleneglycol, etc. to form an oily injection.

An oral administration preparation can be prepared by adding excipients (e.g. lactose, sucrose, starch, etc.), disintegrators (e.g. starch, calcium carbonate), binders (e.g. starch, arabic gum, carboxymethylcellulose, polyvinyl pyrrolidone, hydroxypropylcellulose, etc.) and lubricants (e.g. talc, magnesium stearate, polyethylene glycol 6000, etc.) to the present compound (I), subjecting the mixture to compression molding and optionally masking of taste or coating with a per se known method for the purpose of imparting an enteric property or a sustained-release property. As a coating agent, for example, hydroxypropylmethylcellulose, ethylcellulose, hydroxymethylcellulose, hydroxypropylcellulose, polyoxyethyleneglycol, Tween 80, Pluronic P68, cellulose acetate phthalate, hydroxypropylmethylcellulose phthalate, hydroxymethylcellulose acetate succinate, Eudragit (manufactured by Rohm GmbH & Co. KG, Germany, copolymer of methacrylic acid and acrylic acid) and pigment (e.g. titanium oxide, iron oxide red, etc.) can be used.

The compound (I) of the present invention can be used as a solid, semi-solid or liquid external preparation. For example, the solid external preparation can be prepared by using the present compound (I) as it is, or adding excipients (e.g. glycol, mannitol, starch, microcrystalline cellulose, etc.), thickeners (e.g. natural gums, cellulose derivatives, acrylic polymer, etc.), etc. to the present compound (I), followed by mixing to form a powdered composition. In case of the semi-solid external preparation, it is preferable to use as an aqueous or oily gel agent or an ointment. In case of the liquid external preparation, it can be prepared by forming into an oily or aqueous suspension in nearly the same manner as in case of the injection. To the solid, semi-solid or aqueous external preparation, pH adjustors (e.g. carbonic acid, phosphoric acid, citric acid, hydrochloric acid, sodium hydroxide, etc.) and preservatives (e.g. paraoxybenzoates, chlorobutanol, benzalkonium chloride, etc.) may be added. Specifically, an ointment containing vaseline, lanoline, etc. as a base, and about 0.1 to 100 mg of the present compound (I) can be used for sterilization or disinfection of skin or mucosa.

The present compound (I) can be formed into an oily or aqueous solid, semi-solid or liquid suppository. In case of preparing the suppository, examples of the oily base include glyceride of higher fatty acid [e.g. cacao butter, Witepsol (manufactured by Dynamite Nobel Company), etc.], medium chain length fatty acid [e.g. migriolic acid (manufactured by Dynamite Nobel Company), etc. ] and vegetable oil [e.g. sesame oil, soy bean oil, cotton seed oil]. Examples of the aqueous base include polyethylene glycols, propylene glycols, etc. and examples of the aqueous gel base include natural gums, cellulose derivatives, vinyl polymers, acrylic polymers, etc.

The dose of the present compound (I) varies depending on the infecting condition and administering route, etc. In case of administering orally to adult (weight 50 kg) patients for the purpose of treating Candidiasis, the dose is about 0.01 to 100 mg/kg/day, preferably about 0.1 to 50 mg/kg/day. More preferably, the dose is about 0.5 to 10 mg/kg/day.

Two or more compounds of the present invention can be used in the preparation of the present invention, and also the compound of the present invention can be used in combination with one or more compound having antifungal activity other than the compound of the present invention. When using the present compound (I) as an agricultural antifungal agent, the present compound (I) is dissolved or suspended in a suitable liquid carrier (e.g. solvent), or mixed with or adsorbed to a suitable solid carrier (e.g. diluent, bulking agent, etc.) and, if necessary, emulsifiers, suspension, spreading agents, osmotic agents, wetting agents, mucilages, stabilizers, etc. are added to form an emulsion, hydrate, powder, granule, etc. These preparations can be prepared by a per se known method. In case of the control of rice blight, an amount of the compound (I) of the present invention used is preferably from about 25 to 150 g, more preferably from about 40 to 80 g per are of the paddy field. The compound of the present invention can be used in combination with other agricultural antifungal agent.

As the liquid carrier, for example, water, alcohols (e.g. methyl alcohol, ethyl alcohol, n-propyl alcohol, isopropyl alcohol, ethylene glycol, etc.), ethers (e.g. dioxane, tetrahydrofuran, etc.), aliphatic hydrocarbons (e.g. kerosene, kerosene oil, fuel oil, etc.), aromatic hydrocarbons (e.g. benzene, toluene, etc.), halogenated hydrocarbon (e.g. methylene chloride, chloroform, etc.), acid amides (e.g. dimethylformamide, dimethylacetamide, etc.), esters (e.g. ethyl acetate, butyl acetate, etc.) and nitrites (e.g. acetonitrile, propionitrile, etc.) can be used, and these liquid carriers can be used alone or in combination thereof at a suitable proportion.

As the solid carrier, for example, vegetable flours (e.g. soy bean flours, tobacco flours, wheat flours, etc. mineral powders (e.g. kaolin, bentonite, etc.), alumina, sulfur powder, active carbon, etc. can be used, and these solid carriers can be used alone or in combination thereof in a suitable proportion.

BEST MODE FOR CARRYING OUT THE INVENTION

The following Reference Examples, Examples, Preparation Examples and Experimental Examples illustrate the present invention in detail, but are not to be construed to limit the scope thereof.

$^1$H-NMR spectrum is measured by a Varian Gemini 200 (200 MHz) type spectrometer using tetramethylsilane as an internal standard, and all δ values were represented by ppm. The numerical value described in ( ) for the mixed solvent is a volume mixing ratio of each solvent. "%'s" are by weight unless otherwise stated. A ratio of the solvent in silica gel chromatography represents a volume ratio of solvents to be mixed.

The symbols in the Examples have the following meanings.

s: singlet, d: doublet, t: triplet, q: quartet, dd: double doublet, tt: triple triplet, m: multiplet, br: broad, J: coupling constant.

Reference Example 1

Tetrahydrofurfuryl alcohol (19.4 g) was dissolved in anhydrous ether (500 ml) and, after adding pyridine (15 g) under ice cooling, chloromethyl chloroformate (25 g) was added dropwise. After the reaction mixture was stirred at room temperature for 17 hours, the deposited pyridine hydrochloride was removed by filtration and the filtrate was washed with ether (50 ml×2). The washings and the filtrate were combined, washed with water (300 ml×2) and then dried over anhydrous magnesium sulfate. The solvent was distilled off under reduced pressure to obtain chloromethyl (2,3,4,5-tetrahydrofurfuryl) carbonate (33.9 g) as a colorless oily product.

$^1$H-NMR(CDCl$_3$) δ: 1.59–1.73(1H,m),1.83–2.11(3H,m), 3.75–3.97(2H,m), 4.11–4.34 (3H,m), 5.74(2H,s).

Chloromethyl (2,3,4,5-tetrahydrofurfuryl) carbonate (3.4 g) and sodium iodide (10.46 g) were added to acetonitrile (70 ml), and then the mixture was heated with stirring at 60° C. for 90 minutes. After the reaction solution was cooled, the solvent was distilled off under reduced pressure, and the residue was partitioned between ether (70 ml) and a saturated sodium chloride aqueous solution (50 ml). The organic layer was washed with an aqueous 5% sodium thiosulfate solution (50 ml), water (50 ml) and a saturated sodium chloride aqueous solution (50 ml) successively, and then dried over anhydrous magnesium sulfate. The solvent was distilled off under reduced pressure to obtain iodomethyl (2,3,4,5-tetrahydrofurfuryl) carbonate (4.8 g) as a pale yellow oily product.

$^1$H-NMR(CDCl$_3$) δ: 1.54–1.73(1H,m),1.84–2.11(3H,m), 3.73–3.96(2H,m),4.10–4.32 (3H,m),5.96(2H,s).

Reference Example 2

Glycerol formal (14 g) was dissolved in anhydrous ether (400 ml) and, after adding pyridine (15 g) at −10° C., a solution of chloromethyl chloroformate (25 g) in anhydrous ether (50 ml) was added dropwise over the period of 10 minutes. After the reaction solution was stirred at room temperature for 20 hours, the deposited pyridine hydrochloride was removed by filtration. The filtrate was washed with a saturated sodium chloride aqueous solution (400 ml×2), and then dried over anhydrous magnesium sulfate. The residue obtained by distilling off the solvent under reduced pressure was purified by subjecting to silica gel chromatography (eluent: ethyl acetate/hexane=1/5→ethyl acetate/hexane=1/3) to obtain chloromethyl (1,3-dioxan-5-yl) carbonate (1.7 g) as a colorless oily product.

$^1$H-NMR(CDCl$_3$) δ:4.05 (4 H, d, J=3.2 Hz), 4.67 (1 H, quintet, J=3.2 Hz), 4.82 (1 H, d, J=6.2 Hz), 4.95 (1 H, d, J=6.2 Hz), 5.75 (2 H, s).

The compound obtained above (1.7 g) and sodium iodide (5.1 g) were added to acetonitrile (40 ml), and then the mixture was stirred with heating at 60° C. for 2 hours. The residue obtained by distilling off the solvent of reaction mixture under reduced pressure was dissolved in ether (100 ml). The solution was washed with an aqueous 5% sodium thiosulfate solution (50 ml), water (50 ml) and a saturated sodium chloride aqueous solution (50 ml) successively, and then dried over magnesium sulfate. The solvent was distilled off under reduced pressure to obtain (1,3-dioxan-5-yl) iodomethyl carbonate (3.2 g) as a pale yellow oily product.

$^1$H-NMR(CDCl$_3$) d :4.04 (4 H, d, J=3.0 Hz), 4.66 (1 H, quintet, J=3.0 Hz), 4.81 (1 H, d, J=6.2 Hz), 4.95 (1 H, d, J=6.2 Hz), 5.97 (2 H, s).

Reference Example 3

(R)-Glycerol acetonide (10 g) was dissolved in anhydrous ether (200 ml) and, after adding pyridine (6.6 g) at −10° C., a solution of chloromethyl chloroformate (10.7 g) in anhydrous ether (20 ml) was added dropwise over the period of 10 minutes. After the reaction mixture was stirred at room temperature for 20 hours, the deposited pyridine hydrochloride was removed by filtration. The filtrate was washed with a saturated sodium chloride aqueous solution (200 ml×2), and then dried over anhydrous magnesium sulfate. The residue obtained by distilling off the solvent under reduced pressure was purified by subjecting to silica gel chromatography (eluent: hexane→ethyl acetate/hexane=1/5→ethyl acetate/hexane=3/5) to obtain chloromethyl [(4S)-2,2-dimethyl-1,3-dioxolan-4-yl]methyl carbonate (17 g) as a colorless oily product.

$^1$H-NMR(CDCl$_3$) δ: 1.37 (3 H, s), 1.44 (3 H, s), 3.80 (1 H, dd, J=8.8, 5.8 Hz), 4.07–4.42 (4 H, m), 5.74 (2 H, s).

The compound obtained above (2 g) and sodium iodide (5.3 g) were added to acetonitrile (40 ml), and then the mixture was stirred with heating at 60° C. for 2 hours. The residue obtained by distilling off the solvent of reaction solution under reduced pressure was dissolved in ether (50 ml). The solution was washed with an aqueous 5% sodium thiosulfate solution (50 ml), water (50 ml), and a saturated sodium chloride aqueous solution (50 ml) successively, and then dried over anhydrous magnesium sulfate. The solvent was distilled off under reduced pressure to obtain [(4S)-2,2-dimethyl-1,3-dioxolan-4-yl]methyl iodomethyl carbonate (2.1 g) as a pale yellow oily product.

$^1$H-NMR(CDCl$_3$) δ: 1.37 (3 H, s) , 1.44 (3 H, s), 3.79 (1 H, dd, J=8.0, 5.0 Hz), 4.06–4.41 (4 H, m), 5.96 (2 H, s).

Reference Example 4

To a solution of benzyl 4-hydroxybutanoate (synthesized by the procedure described in Weber et al., J. Med. Chem, 1991, 34, 2692–2701, 5.0 g) in diethyl ether (100 ml), pyridine (2.3 ml) was added under a nitrogen atmosphere, and chloromethyl chloroformate (3.7 g) was added dropwise at −10° C. The reaction mixture was stirred at room temperature for 20 hours. The reaction mixture was filtered with glass filter and then the filtrate was washed with water and a saturated sodium chloride aqueous solution successively. The organic layer was dried over magnesium sulfate, and then the solvent was distilled off under reduced pressure, and thus the residue was subjected to silica gel column chromatography and eluted with acetone/hexane (1:1 v/v) to obtain chloromethyl (3-benzyloxycarbonylpropyl) carbonate (7.25 g) as a colorless oily product.

$^1$H-NMR(CDCl$_3$) d : 2.02–2.12 (2H, m), 2.49 (2H, t, J=7 Hz), 4.28 (2H, t, J=6 Hz), 5.13 (2H, s), 5.71 (2H, s), 7.36 (5H, s).

To a solution of the compound obtained above (2.5 g) in acetonitrile (67 ml) was added sodium iodide (5.2 g) under a nitrogen atmosphere. The mixture was stirred at 60° C. for 8.5 hours. The solvent was distilled off under reduced pressure, and the residue was dissolved in diethyl ether (100 ml). The solution was washed with an aqueous 5% sodium thiosulfate solution, water, and a saturated sodium chloride aqueous solution successively. The organic layer was dried over sodium sulfate, and then concentrated under reduced pressure to obtain (3-benzyloxycarbonylpropyl) iodomethyl carbonate (2.98 g) as a pale yellow oily product.

$^1$H-NMR(CDCl$_3$) d : 2.01–2.08 (2H, m), 2.49 (2H, t, J=7 Hz), 4.28 (2H, t, J=6 Hz), 5.14 (2H, s), 5.94 (2H, s), 7.36 (5H, s).

Reference Example 5

To the mixture of ethyl (S)-lactate (23.6 g), pyridine (15.8 g) and diethyl ether (400 ml) was added dropwise a solution of chloromethyl chloroformate (25.6 g) in diethyl ether (100 ml) under ice cooling over the period of 40 minutes. After stirring at room temperature for 14 hours, the resulting solid was removed off by filtration. The filtrate was concentrated under reduced pressure and the residue was dissolved in ethyl acetate (250 ml). The solution was washed with water (150 ml×2) and a saturated sodium chloride aqueous solution (150 ml). After drying over anhydrous magnesium sulfate, the solvent was distilled off under reduced pressure to obtain chloromethyl [(1S)-1-(ethoxycarbonyl)ethyl] carbonate (38.5 g) as a colorless liquid.

$^1$H-NMR(CDCl$_3$) δ: 1.30(3H,t,J=7.2 Hz), 1.57(3H,d,J=7.0 Hz), 4.25(2H,q,J=7.2 Hz), 5.07(1H,q,J=7.0 Hz), 5.71 (1H,d,J=6.4 Hz) 5.80(1H,d,J=6.4 Hz).

Reference Example 6

To a mixture of benzyl (S)-lactate (30.6 g), pyridine (13.4 g) and diethyl ether (300 ml), a solution of chloromethyl chloroformate (21.9 g) in diethyl ether (100 ml) was added dropwise under ice cooling over the period of 30 minutes. After stirring at room temperature for 5 hours, the resulting solid was removed off by filtration. The filtrate was concentrated under reduced pressure and the residue was dissolved in ethyl acetate (200 ml). The solution was washed with water (100 ml×2) and a saturated sodium chloride aqueous solution (100 ml). After drying over anhydrous magnesium sulfate, the solvent was distilled off under reduced pressure to obtain [(1S)-1-(benzyloxycarbonyl)ethyl] chloromethyl carbonate (45.0 g) as a colorless liquid.

$^1$H-NMR(CDCl$_3$) δ: 1.57(3H,d,J=7 Hz), 5.07–5.28(3H, m), 5.69(1H,d,J=6 Hz), 5.78(1H,d,J=6 Hz), 7.36(5H,s).

[(1S)-1-(benzyloxycarbonyl)ethyl] chloromethyl carbonate (2.7 g) was dissolved in acetonitrile (4 ml) and sodium iodide (6.0 g) was added. The mixture was stirred at 60° C. for 2 hours under an argon atmosphere. After the reaction mixture was concentrated under reduced pressure, diethyl ether (100 ml) and water (100 ml) were added to the residue. The diethyl ether layer was separated and washed with an aqueous 5% sodium thiosulfate solution (80 ml), water (80 ml), and a saturated sodium chloride aqueous solution (80 ml) successively. After drying over anhydrous magnesium sulfate, the solvent was distilled off under reduced pressure to obtain [(1S)-1-(benzyloxycarbonyl)ethyl] iodomethyl carbonate (3.3 g) as a colorless liquid.

$^1$H-NMR(CDCl$_3$) δ: 1.56(3H,d,J=7 Hz), 5.07–5.29(3H, m), 5.93(1H,d,J=5 Hz), 5.98(1H,d,J=5 Hz), 7.37(5H,s).

Reference Example 7

To a solution of 3-(benzyloxy)propanol (synthesized by a procedure described in Wei et al., J. Org. Chem, 54, 5768–5774 (1989):15.1 g) and pyridine (7.18 g) in diethyl ether (150 ml), a solution of chloromethyl chloroformate (11.7 g) in diethyl ether (50 ml) was added dropwise under ice cooling over the period of 20 minutes. After stirring at room temperature for 15 hours, the resulting solid was removed off by filtration and washed with ethyl acetate (100 ml). The filtrate and the washings were combined, and washed with water (100 ml×2) and a saturated sodium chloride aqueous solution (50 ml). After drying the solution over anhydrous magnesium sulfate, the solvent was distilled off under reduced pressure. The residue was purified by subjecting to silica gel chromatography (silica gel 200 g, eluent: ethyl acetate-hexane=1:4) to obtain [3-(benzyloxy)propyl] chloromethyl carbonate (21.0 g) as a colorless liquid.

$^1$H-NMR(CDCl$_3$) δ: 2.01(2H,quintet,J=6.2 Hz), 3.57(2H, t,J=6.0 Hz), 4.36(2H,t,J=6.4 Hz), 4.51(2H,s), 5.71(2H,s), 7.33(5H,s).

[3-(Benzyloxy)propyl] chloromethyl carbonate (2.0 g) was dissolved in acetonitrile (3 ml), and sodium iodide (4.6 g) was added. The mixture was stirred under a nitrogen atmosphere at 60° C. for 2 hours. The reaction mixture was poured into water (100 ml) and extracted with ethyl acetate (100 ml). The ethyl acetate layer was washed with an aqueous 5% sodium thiosulfate solution (50 ml×2), water (50 ml×2), and a saturated sodium chloride aqueous solution (50 ml). After drying over anhydrous magnesium sulfate, the solvent was distilled off under reduced pressure to obtain [3-(benzyloxy)propyl] iodomethyl carbonate (2.5 g) as a pale yellow liquid.

$^1$H-NMR(CDCl$_3$) δ: 2.00(2H,quintet,J=6.2 Hz), 3.57(2H, t,J=6.0 Hz), 4.36(2H,t,J=6.4 Hz), 4.51(2H,s), 5.94(2H,s), 7.34(5H,s).

Reference Example 8

To a mixture of 2-acetylaminoethanol (20.0 g), pyridine (15.3 g) and tetrahydrofuran (100 ml), a solution of chloromethyl chloroformate (25.2 g) in tetrahydrofuran (50 ml) was added dropwise under ice cooling over the period of 30 minutes. After stirring at room temperature for 16 hours, the resulting solid was removed off by filtration and washed with tetrahydrofuran (30 ml). The filtrate and the washing were combined, and concentrated under reduced pressure. To the residue, ethyl acetate (300 ml) and water (100 ml) were added and the organic layer was separated. The aqueous layer was extracted twice with a mixture of ethyl acetate (150 ml) and tetrahydrofuran (50 ml). The organic layers were combined, washed with a saturated sodium chloride aqueous solution (100 ml), and dried over anhydrous magnesium sulfate. The solvent was distilled off under reduced pressure. The residue was purified by subjecting to silica gel chromatography (silica gel 240 g, eluent: ethyl acetate-hexane=1:1→ethyl acetate) to obtain [2-(acetylamino)ethyl] chloromethyl carbonate (32.4 g) as a colorless oil.

$^1$H-NMR(CDCl$_3$) δ: 2.01(3H,s), 3.58(2H,q,J=6 Hz), 4.32 (2H,t,J=6 Hz), 5.75(2H,s), 5.87(1H,br).

[2-(acetylamino)ethyl] chloromethyl carbonate (5.0 g) was dissolved in acetonitrile (15 ml), and sodium iodide (15.0 g) was added. The mixture was stirred at 60° C. for 2 hours under an argon atmosphere. The reaction mixture was poured into ice water (200 ml) and extracted with ethyl acetate (200 ml). The extract was washed with an aqueous 5% sodium thiosulfate solution (100 ml×2), water (100 ml×2) and a saturated sodium chloride aqueous solution (50 ml) successively. After drying over anhydrous magnesium sulfate, the solvent was distilled off under reduced pressure to obtain [2-(acetylamino)ethyl] iodomethyl carbonate (3.5 g) as a yellow oil.

$^1$H-NMR(CDCl$_3$) δ: 2.00(3H,s), 3.54(2H,q,J=6 Hz), 4.28 (2H,t,J=6 Hz), 5.93(2H,s), 6.12(1H,br).

Reference Example 9

To a mixture of 3-(methoxy)propanol (6.0 g), pyridine (5.3 g) and diethyl ether (50 ml), a solution of chloromethyl chloroformate (8.6 g) in diethyl ether (10 ml) was added dropwise under ice cooling over the period of 15 minutes. After stirring at room temperature for 16 hours, water (100 ml) and ethyl acetate (100 ml) were added, and the organic layer was separated. The organic layer was washed with water (100 ml) and a saturated sodium chloride aqueous solution (50 ml), and after drying over anhydrous magnesium sulfate, the solvent was distilled off under reduced pressure. The residue was purified by subjecting to silica gel chromatography (silica gel 70 g, eluent: ethyl acetate-hexane=1:2) to obtain chloromethyl [3-(methoxy)propyl] carbonate (11.0 g) as a colorless liquid.

$^1$H-NMR(CDCl$_3$) δ: 1.97(2H,quintet,J=6.2 Hz), 3.34(3H, s), 3.47(2H,t,J=6.2 Hz), 4.33(2H,t,J=6.2 Hz), 5.74(2H,s).

Chloromethyl [3-(methoxy)propyl] carbonate (3.7 g) was dissolved in acetonitrile (12 ml), and sodium iodide (12.0 g) was added. The mixture was stirred at 55° C. for 4 hours under an argon atmosphere. The reaction mixture was poured into water (100 ml) and extracted with ethyl acetate (100 ml). The ethyl acetate layer was washed with an aqueous 5% sodium thiosulfate solution (50 ml×2), water (50 ml) and a saturated sodium chloride aqueous solution (50 ml). After drying over anhydrous magnesium sulfate, the solvent was distilled off under reduced pressure to obtain iodomethyl [3-(methoxy)propyl] carbonate (5.0 g) as a pale yellow liquid.

$^1$H-NMR(CDCl$_3$) δ: 1.96(2H,quintet,J=6.2 Hz), 3.35(3H, s), 3.47(2H,t,J=6.2 Hz), 4.33(2H,t,J=6.2 Hz), 5.96(2H,s).

EXAMPLE 1

A mixture of 1-[(1R,2R)-2-(2,4-difluorophenyl)-2-hydroxy-1-methyl-3-(1H-1,2,4-triazol-1-yl)propyl]-3-[4-

(1H-1,2,3-triazol-1-yl)phenyl]-2-imidazolidinone (0.25 g) and chloromethyl pivalate (3.0 g) was stirred for 24 hours at 100° C. After having been cooled, the mixture was diluted with diethyl ether(5 ml), and the resulting powder was collected by filtration. The powder was purified by octadecyl silica (hereinafter briefly referred to as ODS) column chromatography (eluent: methanol/water=3/2) to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-[(2,2-dimethylpropanoyloxy)methyl]-1H-1,2,4-triazolium chloride (Compound 1, 0.10 g) as a white powder.

$^1$H-NMR($d_6$-DSMO) δ: 0.97(3H,d,J=7 Hz), 1.13(9H,s), 3.61~4.10(4H,m), 4.65~4.75(1H,m), 4.89(1H,d,J=14 Hz), 5.13(1H,d,J=14 Hz), 6.17(2H,s), 6.74(1H,s), 6.91~7.01(1H, m), 7.21~7.36(2H,m), 7.82~7.93(4H,m), 7.95(1H,d,J=1.2 Hz), 8.79(1H,d,J=1.2 Hz), 9.11(1H,s), 10.53(1H,s).

EXAMPLE 2

A mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone(0.5 g) and chloromethyl pivalate (3.1 g) was stirred for 2 hours at 100° C. After having been cooled, the mixture was diluted with diisopropyl ether (10 ml), and the resulting powder was collected by filtration. The powder was subjected to silica gel flush chromatography (eluent: ethyl acetate→acetone→acetone/ethanol=10/1→acetone/ethanol=5/1) to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-[(2,2-dimethylpropanoyloxy)methyl]-1H-1,2,4-triazolium chloride (Compound 1, 0.34 g) as a white powder.

EXAMPLE 3

A mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone(0.5 g) and chloromethyl pivalate (4.7 g) was stirred for 5 hours at 100° C. After having been cooled, the mixture was diluted with diisopropyl ether (10 ml), and the resulting powder was collected by filtration. The resulting powder was subjected to CHP-20P column chromatography (eluent: water→5% aqueous solution of acetonitrile→30% aqueous solution of acetonitrile→5% aqueous solution of tetrahydrofuran→10% aqueous solution of tetrahydrofuran→20% aqueous solution of tetrahydrofuran) to give 1-[(2R,3R)-2-(2,4-difluorophenyl)-2-hydroxy-3-[2-oxo-3-[4-[3-(2,2-dimethylpropanoyloxy)methyl-1(1H)-1,2,3-triazolio]phenyl]-1-imidazolidinyl]butyl]-4-[(2,2-dimethylpropanoyloxy)methyl]-1H-1,2,4-triazolium dichloride (Compound 8, 134 mg) as a white powder and Compound 1 (141 mg) as a white powder. Compound 8: $^1$H-NMR($d_6$-DSMO) δ: 0.97(3H,d,J=6.8 Hz), 1.13(9H,s), 1.21(9H,s), 3.63–3.66(1H,m), 3.98–4.15(3H,m), 4.62–4.78 (1H,m), 4.88(1H,d,J=14 Hz), 5.23(1H,d,J=14 Hz), 6.17(2H, s), 6.64(2H,s), 6.88(1H,s), 6.90–7.00(1H,m), 7.21–7.36(2H, m), 7.98(2H,d,J=9.8 Hz), 8.05(2H,d,J=9.8 Hz), 9.10(1H,s), 9.34(1H,d,J=2.0 Hz), 9.68(1H,d,J=2.0 Hz), 10.64(1H,s).

EXAMPLE 4

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.48 g) and acetone (10 ml) was added chloromethyl pivalate (2.9 ml), and the mixture was stirred under reflux. After 88 hours, chloromethyl pivalate (1.45 ml) was added to the mixture. The mixture was further stirred for 14 hours under reflux. The reaction mixture was concentrated under reduced pressure. To the residue was added diethyl ether (8 ml), and the resulting powder was collected by filtration. The powder was subjected to ODS column chromatography (eluent: methanol/water=3/2) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(2,2-dimethylpropanoyloxy)methyl]-1,2,4-triazolium chloride (Compound 2, 0.25 g) as a white powder.

$^1$H-NMR($d_6$-DSMO) δ: 0.97(3H,d,J=7 Hz), 1.13(9H,s), 3.61~4.09(4H,m), 4.65~4.75(1H,m), 4.88(1H,d,J=14 Hz), 5.14(1H,d,J=14 Hz), 6.16(2H,s), 6.75(1H,s), 6.91~7.01(1H, m), 7.21~7.37(2H,m), 7.90(4H,s), 9.10(1H,s), 10.07(1H,s), 10.53(1H,s).

EXAMPLE 5

A mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone(0.5 g), chloromethyl pivalate (15.7 g) and acetonitrile (2.4 g) was stirred for 6.5 hours at 100° C. After having been cooled, the mixture was diluted with diisopropyl ether (10 ml), and the resulting powder was collected by filtration. The powder was subjected to silica gel column chromatography (eluent: ethyl acetate→acetone→acetone/ethanol=10/1→acetone/ethanol=5/1) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(2,2-dimethylpropanoyloxy)methyl]-1H-1,2,4-triazolium chloride(Compound 2, 0.32 g) as a white powder. The above Compound 2 (0.4 g) was crystallized from ethyl acetate (20 ml) to give white crystals (0.3 g) of Compound 2.

Melting point: 196–197° C. (decomposition)

Elemental Analysis: $C_{28}H_{32}ClF_2N_9O_4$ Calcd.(%): C,53.21; H,5.10; N,19.94. Found (%): C,53.17; H,5.15; N,19.76.

EXAMPLE 6

A mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone (0.30 g) and chloromethyl acetate (1.35 g) was stirred for 24 hours at 100° C. The reaction mixture was concentrated under reduced pressure. The residue was subjected to ODS column chromatography (eluent: methanol/water=3/2) to give 4-acetoxymethyl-1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-1H-1,2,4-triazolium chloride (Compound 3, 45 mg) as a white powder.

$^1$H-NMR($d_6$-DSMO) δ: 0.97(3H,d,J=7 Hz), 2.08(3H,s), 3.61~4.08(4H,m), 4.65~4.75(1H,m), 4.86(1H,d,J=14 Hz), 5.11(1H,d,J=14 Hz), 6.07~6.20(2H,m), 6.69(1H,s), 6.96~7.05(1H,m), 7.25~7.36(2H,m), 7.82~7.95(5H,m), 8.78 (1H,s), 9.06(1H,s), 10.46(1H,s).

EXAMPLE 7

To a mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone (0.63 g) and acetonitrile (20 ml) was added chloromethyl isobutylate (1.71 g), and the mixture was stirred for 130 hours under reflux. The reaction mixture was concentrated under reduced pressure. To the residue was added diisopropyl ether (10 ml), and the resulting powder was collected by filtration. The powder was subjected to ODS column chromatography (eluent: methanol/water=3/2), and the eluate was concentrated in vacuo. The residue was dissolved in water (20 ml). The solution was lyophilized to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-[(2-methylpropanoyloxy)methyl]-1H-1,2,4-triazolium chloride (Compound 4, 0.335 g) as a white powder.

$^1$H-NMR($d_6$-DSMO) δ: 97(3H,d,J=7 Hz), 1.07(6H,d,J=7 Hz), 2.59(1H,quintet, J=7 Hz), 3.60~4.09(4H,m), 4.65~4.75 (1H,m), 4.87(1H,d,J=14 Hz), 5.10(1H,d, J=14 Hz), 6.10~6.22(2H,m), 6.69(1H,s), 6.93~7.02(1H,m), 7.23~7.35 (2H,m), 7.82~7.93(4H,m), 7.95(1H,s), 8.78(1H,s), 9.08(1H, s), 10.48(1H,s).

EXAMPLE 8

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.50 g) and acetone (20 ml) was added chloromethyl isobutylate (1.37 g), and the mixture was stirred for 50 hours under reflux. The reaction mixture was concentrated under reduced pressure. To the residue was added diisopropyl ether (10 ml), and the resulting powder was collected by filtration. The powder was subjected to ODS column chromatography (eluent: methanol/water=3/2). The eluate was concentrated in vacuo. The residue was dissolved in water (20 ml). The solution was lyophilized to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(2-methylpropanoyloxy)methyl]-1H-1,2,4-triazolium chloride (Compound 5, 0.15 g) as a white powder.

$^1$H-NMR($d_6$-DSMO) δ: 0.97(3H,d,J=7 Hz), 1.07(6H,d, J=7 Hz), 2.59(1H,quintet, J=7 Hz), 3.61~4.08(4H,m), 4.65~4.75(1H,m), 4.87(1H,d,J=14 Hz), 5.11(1H,d, J=14 Hz), 6.14~6.22(2H,m), 6.69(1H,s), 6.92~7.03(1H,m), 7.22~7.37(2H,m), 7.90(4H,s), 9.09(1H,s), 10.08(1H,s), 10.48(1H,s).

The product (50 mg) was crystallized from saturated aqueous solution of sodium chloride (1 ml) to give white powdery crystals of Compound 5. (41 mg).

Melting point: 217–219° C.(decomposition)

Elemental Analysis: $C_{27}H_{30}ClF_2N_9O_4 \cdot 0.5H_2O$ Calcd (%): C,51.72; H,4.98; N,20.10. Found (%): C,51.79; H,4.83; N,20.04.

EXAMPLE 9

To a mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone (100 mg) and 1-chloroethyl ethyl carbonate (1.0 g) was added acetonitrile (0.5 ml), and the mixture was stirred for 60 hours at 85° C. After having been cooled, the mixture was diluted with diisopropyl ether (4 ml), and the resulting powder was collected by filtration. The powder was subjected to ODS column chromatography (eluent: methanol/water=3/2). The eluate was concentrated in vacuo. The residue was dissolved in water (10 ml) and lyophilized to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-[1-(ethoxycarbonyloxy)ethyl]-1H-1,2,4-triazolium chloride (Compound 6, 36 mg) as a white powder.

$^1$H-NMR($d_6$-DSMO) δ: 0.97(3H,d,J=7 Hz), 1.21,1.22 (3H,t,J=7 Hz), 1.80(3H,d, J=6 Hz), 3.61~4.25(6H,m), 4.63~5.09(3H,m), 6.67~6.83(2H,m), 6.94~7.03(1H,m), 7.21~7.37(2H,m), 7.82~8.05(5H,m), 8.79(1H,s), 9.22(0.5H, s), 9.27(0.5H,s), 10.70(0.5H,s), 10.80(0.5H,s).

EXAMPLE 10

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.61 g) and 1-chloroethyl ethyl carbonate (3.7 g) was added acetonitrile (1 ml), and the mixture was stirred for 38 hours at 95° C. The reaction mixture was concentrated under reduced pressure. To the residue was added diisopropyl ether (10 ml), and the resulting powder was collected by filtration. The powder was subjected to ODS column chromatography (eluent: methanol/water=3/2). The eluate was concentrated in vacuo. The residue was dissolved in water (10 ml), and lyophilized to give 1-[(2R,3R)-2-(2,4-difluorophenyl)-2-hydroxy-3-[2-oxo-3-[4-(1H-tetrazol-1-yl)phenyl]-1-imidazolidinyl] butyl]-4-[1-(ethoxy-carbonyloxy)ethyl]-1H-1,2,4-triazolium chloride (Compound 7,90 mg) as a white powder.

$^1$H-NMR($d_6$-DSMO) δ: 0.97(3H,d,J=7 Hz), 1.21,1.22 (3H,t,J=7 Hz), 1.79,1.80(3H, d,J=6 Hz), 3.62~4.23(6H,m), 4.65~5.10(3H,m), 6.69~6.82(2H,m), 6.94~7.04(1H,m), 7.26~7.38(2H,m), 7.90(4H,s), 9.23(0.5H,s), 9.27(0.5H,s), 10.08(1H,s), 10.72(0.5H,s), 10.82(0.5H,s).

EXAMPLE 11

A mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone(0.5 g), chloromethyl isopropyl carbonate (3.2 g) and acetonitrile (1 ml) was stirred for 25 hours at 100° C. After having been cooled, the mixture was diluted with diisopropyl ether (10 ml), and the resulting powder was collected by filtration and subjected to the silica gel column chromatography (eluent: ethyl acetate→acetone→acetone/ethanol=10/1→acetone/ethanol=5/1). Solvent was distilled off under reduced pressure, and residue was subjected to crystallization from ethyl acetate. The crystals were dissolved in water (10 ml). The aqueous solution was lyophilized to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-[(isopropoxycarbonyloxy)methyl]-1H-1,2,4-triazolium chloride (Compound 9, 0.18 g) as a white powder.

$^1$H-NMR($d_6$-DSMO) δ: 0.98(3H,d,J=7 Hz), 1.24(6H,d,J= 6.4 Hz), 3.52–3.67(1H,m), 3.93–4.00(3H,m), 4.69(1H,q,J=7 Hz), 4.80(1H,quintet,J=6.4 Hz), 4.88(1H,d, J=13.8 Hz), 5.05(1H,d,J=13.8 Hz), 6.12(1H,d,J=10.8 Hz), 6.20(1H,d,J= 10.8 Hz), 6.98–7.03(1H,m), 7.23–7.36(2H,m), 7.84(2H,d, J=8 Hz), 7.91(2H,d,J=8 Hz), 7.94 (1H,d,J=1H,z), 8.77(1H, d,J=1H,z), 9.10(1H,s), 10.38(1H,s). The lyophilized product of compound 9 above obtained (0.05 g) was recrystallized from acetonitrile (3 ml) to give white crystals (0.01 g) of Compound 9.

Elemental Analysis: $C_{28}H_{31}ClF_2N_8O_5 \cdot H_2O$ Calcd.: (%): C,51.65; H,5.11; N,17.21. Found: (%): C,51.64; H,4.68; N,17.06.

EXAMPLE 12

To a mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone (0.5 g) and acetonitrile (10 ml) was added bromomethyl acetate (0.1 ml), and the mixture was stirred for 24 hours at 50° C. The reaction mixture was purified by silica gel flush chromatography (silica gel: 25 g, eluent: ethyl acetate→acetone→acetone/ethanol=10/1). The residue purified was crystallized from ethanol to give 4-acetoxymethyl-1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-1H-1,2,4-triazolium bromide (Compound 10, 0.135 g) as colorless crystals.

$^1$H-NMR(d$_6$-DMSO) δ: 0.98(3H,d,J=7 Hz), 2.08(3H,s), 3.62–4.08(4H,m), 4.66–4.75 (1H,m), 4.87(1H,d,J=14 Hz), 4.99(1H,d,J=14 Hz), 6.07–6.21(2H,m), 6.34(1H,s), 6.96–7.07(1H,m), 7.24–7.35(2H,m), 7.83–7.94(5H,m), 8.80 (1H,s), 9.09(1H,s), 10.24(1H,s).

EXAMPLE 13

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.5 g) and acetonitrile (10 ml) was added bromomethyl acetate (0.2 ml), and the mixture was stirred for 16 hours at 50° C. The reaction mixture was purified by silica gel flush chromatography (silica gel: 25 g, eluent: ethyl acetate→acetone→acetone/ethanol=10/1). The residue purified was crystallized from ethanol to give 4-acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium bromide (Compound 11, 0.39 g) as colorless crystals.

$^1$H-NMR(d$_6$-DMSO) δ: 0.99(3H,d,J=7 Hz), 2.09(3H,s), 3.64–4.08(4H,m), 4.68–4.72 (1H,m), 4.86(1H,d,J=14 Hz), 5.01(1H,d,J=14 Hz), 6.07–6.21(2H,m), 6.35 (1H,s), 7.00–7.09(1H,m), 7.28–7.38(2H,m), 7.91(4H,s), 9.10(1H,s), 10.08 (1H,s), 10.28(1H,s)

EXAMPLE 14

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.5 g) and acetonitrile (10 ml) was added iodomethyl (2,3,4,5-tetrahydrofurfuryl) carbonate (0.594 g), and the mixture was stirred for 15 hours at 50° C. The reaction mixture was subjected to silica gel flush chromatography (eluent: ethyl acetate→acetate→acetone/ethanol=10/1), and the fraction containing the desired compound was concentrated under reduced pressure. The residue was subjected to ODS column chromatography (eluent:methanol/water=3/2). The fraction containing the desired compound was concentrated and the residue was lyophilized to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(2,3,4,5-tetrahydrofurfuryl)oxycarbonyloxymethyl]-1H-1,2,4-triazolium iodide (Compound 30, 0.4 g) as a colorless powder. The product was dissolved in water (15 ml), and the solution was subjected to ion-exchange resin [Dowex 1×8 (Cl$^-$ type)]. The fraction containing the desired compound was concentrated under reduced pressure, and lyophilized to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(2,3,4,5-tetrahydrofurfuryl)oxycarbonyloxymethyl]-1H-1,2,4-triazolium chloride (Compound 21, 0.24 g) as a colorless powder.

$^1$H-NMR(d$_6$-DMSO) δ: 0.97(3H,d,J=7 Hz), 1.52–1.99 (4H,m), 3.61–4.17(9H,m), 4.67–4.82(1H,m), 4.86(1H,d,J= 14 Hz), 5.10(1H,d,J=14 Hz), 6.11–6.25(2H,m), 6.65(1H,s), 6.69–7.06(1H,m), 7.28–7.39(2H,m), 7.90(4H,s), 9.10(1H,s), 10.08(1H,s), 10.47(1H,s)

EXAMPLE 15

4-Acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium bromide (Compound 11, 0.81 g) was subjected to ion-exchange resin [Dowex 1×8 (Cl$^-$ type)] (eluent: water). The eluate was lyophilized to give 4-acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 12, 0.61 g) as a white powder.

$^1$H-NMR (d$_6$-DMSO) δ: 0.97 (3 H, d, J=7.4 Hz), 2.08 (3 H, s), 3.62–3.66 (1H, m), 3.90–4.07 (3 H, m), 4.69 (1H, q, J=7.4 Hz), 4.85 (1H, d, J=14.6 Hz), 5.04 (1H, d, J=14.6 Hz), 6.09 (1H, d, J=11H,z), 6.16 (1H, d, J=11H,z), 6.55 (1H, s), 6.98–7.06 (1H, m), 7.23–7.38 (2 H, m), 7.90 (4 H, s), 9.06 (1H, s), 10.06 (1H, s), 10.34 (1H, s).

The lyophilized product (1.1 g) of Compound 12 obtained above was recrystallized from ethanol (20 ml) to give Compound 12 as white crystals (1 g).

Elemental Analysis: $C_{25}H_{26}ClF_2N_9O_4$

Calcd.: (%): C, 50.89; H, 4.44; N, 21.37, Cl, 6.01.

Found: (%): C, 50.61; H, 4.38; N, 21.24, Cl, 5.80.

The crystals (0.63 g) of Compound 12 was dissolved in water (10 ml), and the solution was allowed to stand overnight at 0° C. to give the hydrate (0.61 g) of Compound 12 as white crystals.

Elemental Analysis: $C_{25}H_{26}ClF_2N_9O_4 \cdot H_2O$

Calcd.: (%): C, 49.39; H, 4.64; N, 20.73.

Found: (%): C. 49.56; H, 4.64; N, 20.85.

EXAMPLE 16

4-Acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium bromide (Compound 11, 0.5 g) was dissolved in tetrahydrofuran (100 ml). To the solution was added saturated aqueous solution (100 ml) of sodium chloride. The mixture was shaken and the organic layer was separated. The shaking with sodium chloride solution followed by separation of the organic layer was repeated five times. The organic layer was dried over magnesium sulfate and the solvent was distilled off. The residue was recrystallized from ethanol (5 ml) to give 4-acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 12, 0.28 g) as white crystals. The physicochemical properties of this product were identical with those of the crystals of Compound 12 obtained by crystallization from ethanol in Example 15.

EXAMPLE 17

A mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (1 g), iodomethyl acetate (0.8 g) and acetonitrile (15 ml) was stirred for 15 hours at 50–55° C. The solvent was distilled off, and the residue was dissolved in tetrahydrofuran (100 ml). The solution was washed once with saturated aqueous solution (100 ml) of sodium chloride containing a small amount of sodium thiosulfate, followed by washing for four times with saturated aqueous solution (100 ml) of sodium chloride. The organic layer was dried over magnesium sulfate, and the solvent was distilled off under reduced pressure. The residue was subjected to silica gel chromatography (eluent: ethyl acetate→acetone→acetone/ethanol=10/1→acetone/ethanol=5/1). The solvent was distilled off, and the residue was crystallized from ethanol (10 ml) to give 4-acetoxymethyl-1-[(2R,3R)-2-(2,4-difluorophenyl)-2- hydroxy-3-[2-oxo-3-[4-(1H-tetrazol-1-yl)phenyl]-1-imidazolidinyl]butyl]-1H-1,2,4-triazolium chloride (Compound 12, 0.44 g) as white crystals. The physicochemical properties of this product were identical with those of the crystals of Compound 12 obtained by crystallization from ethanol in Example 15.

EXAMPLE 18

4-Acetoxymethyl-1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-1H-1,2,4-triazolium bromide (Compound 10, 0.03 g) was subjected to ion-exchange resin [Dowex 1×8 (Cl$^-$ type)] (eluent: water). The eluate was lyophilized to give 4-acetoxymethyl-1-[(2R,3R)-2-(2,4-difluorophenyl)-2-hydroxy-3-[2-oxo-3-[4-(1H-1,2,3-triazol-1-yl)phenyl]-1-imidazolidinyl]butyl)-1H-1,2,4-triazolium chloride (Compound 3, 0.02 g) as a white powder.

Elemental Analysis: $C_{26}H_{27}ClF_2N_8O_4 \cdot 2H_2O$

Calcd.: C, 49.96; H, 5.00; N, 17.93; Cl, 5.67.

Found: C, 49.98; H, 4.57; N, 17.95; Cl, 6.04.

EXAMPLE 19

A mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.5 g), chloromethyl propyl carbonate (3.2 g) and acetonitrile (1 ml) was stirred for 12 hours at 100° C. After having been cooled, the mixture was diluted with diisopropyl ether (10 ml), and the resulting powder was collected by filtration. The powder was subjected to silica gel chromatography (eluent: ethyl acetate→acetone→acetone/ethanol=10/1→acetone/ethanol=5/1). The solvent was distilled off, and the residue was subjected to ODS column chromatography (eluent: methanol/water=3/2) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-propoxycarbonyloxymethyl-1H-1,2,4-triazolium chloride (Compound 19, 0.02 g) as a white powder.

$^1$H-NMR (d$_6$-DMSO) δ: 0.88 (3 H, t, J=7.8 Hz), 0.97 (3 H, d, J=7.0 Hz), 1.62 (2 H, tq, J=7.8 Hz), 3.63–3.67 (1H, m), 3.80–4.05 (3 H, m), 4.09 (2 H, t, J=7.8 Hz), 4.69 (1H, q, J=7.0 Hz), 4.88 (1H, d, J=14.4 Hz), 5.05 (1H, d, J=14.4 Hz), 6.13 (1H, d, J=10.6 Hz), 6.21 (1H, d, J=10.6 Hz), 6.52 (1H, s), 6.94–7.02 (1H, m), 7.24–7.33 (2 H, m), 7.90 (4 H, s), 9.10 (1H, s), 10.05 (1H, s), 10.39 (1H, s).

EXAMPLE 20

A mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (1 g), iodomethyl propyl carbonate (0.9 g) and acetonitrile (15 ml) was stirred for 12 hours at 50–55° C. The mixture was subjected to silica gel chromatography (eluent: ethyl acetate/hexane=5/1→ethyl acetate→acetone→acetone/ethanol=10/1→acetone/ethanol=5/1) and then ODS column chromatography (eluent: methanol/water=3/2) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-propoxycarbonyloxymethyl-1H-1,2,4-triazolium iodide (Compound 20, 1 g) as a pale yellow powder.

$^1$H-NMR (d$_6$-DMSO) δ: 0.88 (3 H, t, J=7.2 Hz), 0.98 (3 H, d, J=7.2 Hz), 1.61 (2 H, tq, J=7.2 Hz), 3.50–3.70 (1H, m), 3.84–4.13 (3 H, m), 4.09 (2 H, t, J=7.2 Hz), 4.68 (1H, q, J=7.2 Hz), 4.86 (1H, d, J=13.8 Hz), 4.96 (1H, d, J=13.8 Hz), 6.12 (1H, d, J=11H,z), 6.20 (1H, d, J=11H,z), 6.33 (1H, s), 6.97–7.07 (1H, m), 7.21–7.38 (2 H, m), 7.90 (4 H, s), 9.11 (1H, s), 10.05 (1H, s), 10.21 (1H, s).

EXAMPLE 21

1-[(2R,3R)-2-(2,4-Difluorophenyl)-2-hydroxy-3-[2-oxo-3-[4-(1H-tetrazol-1-yl)phenyl]-1-imidazolidinyl]butyl]-4-propoxycarbonyloxymethyl-1H-1,2,4-triazolium iodide (Compound 20, 0.3 g) was dissolved in a mixture of tetrahydrofuran and ethyl acetate (3/1) (100 ml), and the solution was washed four times with saturated aqueous solution (50 ml) of sodium chloride. The organic layer was dried over magnesium sulfate, and the solvent was distilled off. The residue was crystallized from ethanol/acetone to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-propoxycarbonyloxymethyl-1H-1,2,4-triazolium chloride (Compound 19, 0.09 g) as a white powder.

Elemental Analysis: $C_{27}H_{30}ClF_2N_9O_5 \cdot 0.5H_2O$ Calcd. (%): C, 50.43; H, 4.86; N, 19.60; Cl, 5.51. Found (%): C, 50.25; H, 4.71; N, 19.31; Cl, 5.42.

EXAMPLE 22

To a mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone (0.80 g) and chloromethyl propanate (4.07 g) was added acetonitrile (1.6 ml), and the mixture was stirred for 12 hours at 100° C. under an argon atmosphere. The reaction mixture was concentrated under reduced pressure, and to the residue was added diisopropyl ether (8 ml). The resulting powder was collected by filtration. The powder was subjected to silica gel flush chromatography (eluent: ethyl acetate→acetone→acetone/ethanol=9/1→4/1), and a fraction containing the desired compound was concentrated under reduced pressure. The residue was subjected to ODS column chromatography (eluent: methanol/water=3/2). The eluate was concentrated in vacuo, and the residue was dissolved in water (10 ml). The solution was lyophilized to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-propanoyloxymethyl-1H-1,2,4-triazolium chloride (Compound 13, 0.11 g) as a white powder.

$^1$H-NMR(d$_6$-DSMO) δ: 0.92–1.12(6H,m) , 2.25–2.55 (2H,m), 3.60–4.10(4H,m), 4.64–4.75(1H,m), 4.86(1H,d,J= 14 Hz), 5.08(1H,d,J=14 Hz), 6.09–6.21(2H,m), 6.64(1H,s), 6.96–7.06(1H,m), 7.22–7.42(2H,m), 7.80–8.02(5H,m), 8.80 (1H,brs), 9.07(1H,s), 10.42(1H,s).

EXAMPLE 23

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.80 g) and chloromethyl propanate (4.07 g) was added acetonitrile (1.6 ml), and the mixture was stirred for 10 hours at 100 ° C. under an argon atmosphere. The reaction mixture was concentrated under reduced pressure, and to the residue was added diisopropyl ether (8 ml). The resulting powder was collected by filtration. The powder was subjected to silica gel flush chromatography (eluent: ethyl acetate→acetone→acetone/ethanol=9/1→5/1), and the fraction containing the desired compound was concentrated under reduced pressure. The residue was subjected to ODS column chromatography (eluent: methanol/water=3/2). The eluate was concentrated in vacuo, and the residue was dissolved in water (10 ml). The solution was lyophilized to give 1-[(2R,3R)-2-(2,4-difluorophenyl)-2-hydroxy-3-[2- oxo-3-[4-(1H-tetrazol-1-yl)phenyl]-1-imidazolidinyl]butyl]-4-propanoyloxymethyl-1H-1,2,4-triazolium chloride (Compound 14, 0.04 g) as a white powder.

$^1$H-NMR($d_6$-DSMO) δ: 0.97(3H,d,J=7 Hz), 1.01(3H,t,J=7.4 Hz), 2.38(2H,q,J=7.4 Hz), 3.61~4.09(4H,m), 4.65~4.75 (1H,m), 4.86(1H,d,J=14 Hz), 5.08(1H,d,J=14 Hz), 6.11(1H,d,J=11H,z), 6.19(1H,d,J=11H,z), 6.61(1H,s), 6.96~7.06(1H,m), 7.25~7.49(2H,m), 7.90(4H,s), 9.07(1H,s), 10.07(1H,s), 10.40(1H,s).

EXAMPLE 24

To a mixture of 1-[(1R,2R)-2-(2,4-difluorophenyl)-2-hydroxy-1-methyl-3-(1H-1,2,4-triazol-1-yl)propyl]-3-[4-(1H-1,2,3-triazol-1-yl)phenyl]-2-imidazolidinone(0.50 g) and chloromethyl ethyl carbonate (2.9 g) was added acetonitrile (0.5 ml), and the mixture was stirred for 22 hours at 100° C. The reaction mixture was concentrated under reduced pressure. To the residue was added diisopropyl ether (10 ml), and the resulting powder was collected by filtration. The powder was subjected to silica gel flush chromatography (eluent: ethyl acetate/acetone=1/1→acetone→acetone/ethanol=9/1→4/1), and the fraction containing the desired compound was concentrated under reduced pressure. The residue was subjected to ODS column chromatography (eluent: methanol/water=3/2). The eluate was concentrated in vacuo, and the residue was dissolved in water(15 ml). The solution was lyophilized to give 1-[(2R,3R)-2-(2,4-difluorophenyl)-2-hydroxy-3-[2-oxo-3-[4-(1H-1,2,3-triazol-1-yl)phenyl]-1-imidazolidinyl]butyl]-4-ethoxycarbonyloxymethyl-1H-1,2,4-triazolium chloride (Compound 15, 0.14 g) as a white powder.

$^1$H-NMR($d_6$-DSMO) δ: 0.97(3H,d,J=7 Hz), 1.22(3H,t, J=7 Hz), 3.60~4.08(4H,m), 4.18(2H,q,J=7 Hz), 4.63–4.73 (1H,m), 4.87(1H,d,J=14 Hz), 5.10(1H,d,J=14 Hz), 6.13(1H, d,J=11H,z), 6.21(1H,d,J=11H,z), 6.65(1H,s), 6.96~7.04(1H, m), 7.24~7.37(2H,m), 7.82~7.95(5H,m), 8.78(1H,d,J=1H, z), 9.09(1H,s), 10.48(1H,s).

EXAMPLE 25

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone(1.31 g) and ethyl iodomethyl carbonate (1.25 g) was added acetonitrile (20 ml) and the mixture was stirred for 14 hours at 60° C. under an argon atmosphere. The reaction mixture was concentrated under reduced pressure and the residue was submitted to silica gel flush chromatography (eluent: ethyl acetate→acetone→acetone/ethanol=4/1). The fraction containing the desired compound was concentrated under reduced pressure. The residue was subjected to ODS column chromatography (eluent: methanol/water=3/2) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-ethoxycarbonyloxymethyl-1H-1,2,4-triazolium iodide (Compound 17, 1.1 g) as a pale yellow powder.

$^1$H-NMR($d_6$-DSMO) δ: 0.99(3H,d,J=7 Hz), 1.23(3H,t, J=7 Hz), 3.64–4.05(4H,m), 4.19(2H,q,J=7 Hz), 4.64–4.74 (1H,m), 4.87(1H,d,J=14 Hz), 4.97(1H,d,J=14 Hz), 6.13(1H, d,J=11H,z), 6.21(1H,d,J=11H,z), 6.33(1H,br), 6.99–7.07 (1H,m), 7.22–7.39(2H,m), 7.91(4H,s), 9.12(1H,s), 10.06 (1H,s), 10.23(1H,s).

EXAMPLE 26

1-[(2R,3R)-2-(2,4-Difluorophenyl)-2-hydroxy-3-[2-oxo-3-[4-(1H-tetrazol-1-yl)phenyl]-1-imidazolidinyl]butyl]-4-ethoxycarbonyloxymethyl-1H-1,2,4-triazolium iodide (Compound 17, 1.10 g) was subjected to ion-exchange chromatography (DOWEX 1×8, Cl⁻ type, 300 ml), and the fraction containing the desired compound was concentrated under reduced pressure. The residue was recrystallized from ethanol to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-ethoxycarbonyloxymethyl-1H-1,2, 4-triazolium chloride (Compound 16, 0.70 g) as colorless powdery crystals.

$^1$H-NMR($d_6$-DSMO) δ: 0.97(3H,d,J=7 Hz), 1.22(3H,t, J=7 Hz), 3.60–4.08(4H,m), 4.18(2H,q,J=7 Hz), 4.63–4.73 (1H,m), 4.87(1H,d,J=14 Hz), 5.10(1H,d,J=14 Hz), 6.13(1H, d,J=11H,z), 6.21(1H,d,J=11H,z), 6.66(1H,s), 6.96–7.04(1H, m), 7.24–7.36(2H,m), 7.90(4H,s), 9.09(1H,s), 10.07(1H,s), 10.48(1H,s).

EXAMPLE 27

A mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (0.5 g), chloromethyl isopropyl carbonate (3.17 g) and acetonitrile (1 ml) was stirred for 6 hours at 100° C. After having been cooled, the mixture was diluted with diisopropyl ether (10 ml). The resulting powder was collected by filtration. The powder was subjected to silica gel chromatography (eluent: ethyl acetate→acetone→acetone/ethanol=10/1→acetone/ethanol=5/1). The solvent was distilled off, and the residue was crystallized from ethanol/acetone to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-(isopropoxycarbonyloxy)methyl-1H-1,2,4-triazolium chloride (Compound 18, 110 mg) as white powdery crystals.

$^1$H-NMR ($d_6$-DMSO) δ: 0.98 (3 H, d, J=7.4 Hz), 1.24 (6 H, d, J=6.2 Hz), 3.62–3.66 (1H, m), 3.98–4.0 (3 H, m), 4.69 (1H, q, J=7.4 Hz), 4.80 (1H, quintet, J=6.2 Hz), 4.87 (1H, d, J=14.4 Hz), 5.04 (1H, d, J=14.4 Hz), 6.11 (1H, d, J=11H,z), 6.19 (1H, d, J=11H,z), 6.51 (1H, s), 6.96–7.03 (1H, m), 7.22–7.38 (2 H, m), 7.90 (4 H, s), 9.10 (1H, s), 10.06 (1H, s), 10.36 (1H,s).

EXAMPLE 28

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (2.5 g) and (1,3-dioxan-5-yl) iodomethyl carbonate (3 g) was added acetonitrile (40 ml), and the mixture was stirred for 12 hours at 50–55° C. The mixture was subjected to silica gel chromatography (eluent: ethyl acetate/hexane=1/1→ethyl acetate/hexane=10/1→ethyl acetate→acetone→acetone/ethanol=5/1) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(1,3-dioxan-5-yl)oxycarbonyloxymethyl]-1H-1,2,4-triazolium iodide (Compound 31, 4.22 g) as a yellow powder.

$^1$H-NMR ($d_6$-DMSO) δ: 0.98 (3 H, d, J=7 Hz), 3.55–3.75 (1H, m), 3.87–4.02 (7 H, m), 4.50–4.58 (1H, m.), 4.67–4.93 (5 H, m), 6.16 (1H, d, J=11H,z), 6.24 (1H, d, J=11H,z), 6.33 (1H, s), 6.97–7.07 (1H, m), 7.21–7.39 (2 H, m), 7.90 (4 H, s), 9.12 (1H, s), 10.05 (1H, s), 10.23 (1H, s).

EXAMPLE 29

1-[(2R,3R)-2-(2,4-Difluorophenyl)-2-hydroxy-3-[2-oxo-3-[4-(1H-tetrazol-1-yl)phenyl]-1-imidazolidinyl]butyl]-4-[(1–3-dioxan-5-yl)oxycarbonyloxymethyl]-1H-1,2,4- triazolium iodide (Compound 31, 1 g) was subjected to ion-exchange resin [Dowex 1×8 (Cl⁻ type)] (eluent: water), and the eluate was lyophilized to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(1,3-dioxan-5-yl)oxycarbonyloxymethyl]-1H-1,2,4-triazolium chloride (Compound 22, 0.23 g) as a white powder.

¹H-NMR (d₆-DMSO) δ: 0.97 (3 H, d, J=6.6 Hz), 3.63–3.66 (1H, m), 3.87–4.02 (7 H, m), 4.52–4.59 (1H, m), 4.60–5.11 (5 H, m), 6.17 (1H, d, J=11H,z), 6.25 (1H, d, J=11H,z), 6.59 (1H, s), 6.97–7.04 (1H, m), 7.23–7.40 (2 H, m), 7.90(4H,s),9.11 (1H, s), 10.06 (1H, s), 10.44 (1H, s).

The lyophilized product (0. 15 g) of Compound 22 obtained above was crystallized from ethanol(20 ml) to give white crystals of Compound 22 (0. 14 g).

Elemental Analysis: C₂₈H₃₀ClF₂N₉O₇
Calcd.(%): C,49.60; H,4.46; N,18.59.
Found (%): C,49.60; H,4.46; N,18.40.

EXAMPLE 30

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone(0.50 g) and chloromethyl [(1S)-1-(ethoxycarbonyl)ethyl] carbonate (1.09 g) was added acetonitrile (5 ml), and the mixture was stirred for 68 hours at 95° C. The reaction mixture was concentrated under reduced pressure. To the residue was added diisopropyl ether (6 ml), and the resulting powder was collected by filtration. The powder was subjected to silica gel flush chromatography (eluent: ethyl acetate→ethyl acetate/acetone=1/1→acetone→acetone/ethanol=5/1). The fraction containing the desired compound was concentrated under reduced pressure. The residue was subjected to ODS column chromatography (eluent: methanol/water=3/2). The eluate was concentrated in vacuo and dissolved in water (50 ml). The solution was lyophilized to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[[(1S)-1-ethoxycarbonylethoxy]carbonyloxymethyl]-1H-1,2,4-triazolium chloride (Compound 23,0.22 g) as a white powder.

¹H-NMR(d₆-DMSO) δ:0.98(3H,d,J=7 Hz), 1.17(3H,t,J=7 Hz), 1.43(3H,d,J=7 Hz), 3.60–4.08(4H,m), 4.14(2H,q,J=7 Hz), 4.65–4.75(1H,m), 4.86(1H,d,J=14 Hz), 5.02(1H,q,J=7 Hz), 5.11(1H,d,J=14 Hz), 6.24(2H,s), 6.65(1H,s), 6.95–7.05 (1H,m), 7.25–7.39(2H,m), 7.90(4H,s), 9.11(1H,s), 10.07 (1H,s), 10.52(1H,s).

EXAMPLE 31

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (1.0 g) and [(1S)-1-(benzyloxycarbonyl)ethyl] iodomethyl carbonate (1.53 g) was added acetonitrile (15 ml), and the mixture was stirred for 12 hours at 60° C. under an argon atmosphere. The reaction mixture was concentrated under reduced pressure and the residue was subjected to silica gel flush chromatography (eluent: ethyl acetate→acetone→acetone/ethanol=4/1). The fraction containing the desired compound was concentrated under reduced pressure. The residue was subjected to ODS column chromatography (eluent: methanol/water=3/2), and subjected to ion-exchange chromatography (DOWEX 1×8, Cl⁻ type). The fraction containing the desired compound was concentrated under reduced pressure to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[[(1S)-1-(benzyloxycarbonylethoxy]carbonyloxymethyl]-1H-1,2,4-triazolium chloride (Compound 24, 0.25 g) as a white powder.

¹H-NMR(d₆-DMSO) δ:0.97(3H,d,J=7.0 Hz), 1.45(3H,d, J=6.6 Hz), 3.60–4.08(4H,m), 4.65–4.78(1H,m), 4.85(1H,d, J=14 Hz), 5.07–5.18(4H,m), 6.23(2H,s), 6.67(1H,s), 6.95–7.04(1H,m), 7.24–7.37(7H,m), 7.9(4H,s), 9.09(1H,s), 10.07(1H,s), 10.53(1H,s)

EXAMPLE 32

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone(2.0 g) and (3-benzyloxypropyl) iodomethyl carbonate(2.9 g) was added acetonitrile (20 ml), and the mixture was stirred for 20 hours at 50~55° C. under an argon atmosphere. The reaction mixture was concentrated under reduced pressure. The residue was dissolved in a mixture of ethyl acetate (100 ml) and tetrahydrofuran (50 ml). To the solution was added a mixture of saturated aqueous solution of sodium chloride (50 ml) and 5% aqueous solution of sodium thiosulfate (0.1 ml), and the mixture was shaken. The organic layer was washed with saturated aqueous solution of sodium chloride (50 ml) four times. The organic layer was dried over anhydrous magnesium sulfate, and the solvent was distilled off. The residue was subjected to silica gel flush chromatography (eluent: ethyl acetate→acetone→acetone/ethanol=4/1). The fraction containing the desired compound was concentrated under reduced pressure. The residue was subjected to ODS column chromatography (eluent: methanol/water=3/2), and then the eluate was subjected to ion-exchange chromatography (DOWEX 1×8, Cl⁻ type). The fraction containing the desired compound was concentrated under reduced pressure to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(3-benzyloxypropoxy)carbonyloxymethyl]-1H-1,2,4-triazolium chloride (Compound 25, 0.79 g) as a white powder.

¹H-NMR(d₆-DMSO) δ:0.97(3H,d,J=7.2 Hz), 1.89(2H, quintet,J=6.4 Hz), 3.47(2H,t, J=6.2 Hz), 3.60–4.09(4H,m), 4.22(2H,t,J=6.6 Hz), 4.44(2H,s), 4.65–4.75(1H,m), 4.86 (1H,d,J=14 Hz), 5.09(1H,d,14 Hz), 6.12(1H,d,J=11H,z), 6.20(1H,d,J=11H, z), 6.62(1H,s), 6.94–7.04(1H,m), 7.24–7.36(7H,m), 7.9(4H,s), 9.09(1H,s), 10.07 (1H,s), 10.45 (1H,s).

EXAMPLE 33

1-[(2R,3R)-2-(2,4-Difluorophenyl)-2-hydroxy-3-[2-oxo-3-[4-(1H-tetrazol-1-yl)phenyl]-1-imidazolidinyl]butyl]-4-[(3-benzyloxypropoxy)carbonyloxymethyl]-1H-1,2,4-triazolium chloride(Compound 25, 0.66 g) was dissolved in methanol (25 ml), and to the solution were added 1N-hydrochloric acid (0.89 ml) and 10% palladium-carbon (50% wet, 0.33 g). The mixture was stirred for 1.5 hours at room temperature under a hydrogen atmosphere. The catalyst was filtered off, and the filtrate was concentrated under reduced pressure. The residue was subjected to ODS column chromatography (eluent: methanol/water=3/2) and recrystallized from ethanol to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(3-hydroxypropoxy)carbonyloxymethyl]-1H-1,2,4-triazolium chloride (Compound 26, 0.19 g) as colorless powdery crystals.

¹H-NMR(d₆-DSMO) δ:0.98(3H,d,J=7 Hz), 1.74(2H, quintet,J=6 Hz), 3.44(2H,dt, J=6 Hz,5 Hz), 3.60–4.10(4H, m), 4.20(2H,t,J=6 Hz), 4.59(1H,t,J=5 Hz), 4.65–4.75 (1H, m), 4.87(1H,d,J=14 Hz), 5.10(1H,d,J=14 Hz), 6.13(1H,d,J= 11H,z), 6.21(1H, d,J=11H,z), 6.63(1H,s), 6.95–7.05(1H,m), 7.25–7.37(2H,m), 7.89(4H,s), 9.09 (1H,s), 10.06(1H,s), 10.48(1H,s).

EXAMPLE 34

A mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (1.6 g) and iodomethyl [(4S)-2,2-dimethyl-1,3-dioxolan-4-yl]methyl carbonate (2.1 g) was added to acetonitrile (20 ml), and the mixture was stirred for 15 hours at 55° C. The resulting mixture was subjected to silica gel chromatography (eluent: ethyl acetate→acetone→acetone/ethanol=5/1), and then the eluate was subjected to ion-exchange resin (Dowex 1×8, Cl⁻) (eluent: water). The eluate was evaporated in vacuo, and the residue was subjected to ODS column chromatography (eluent: methanol/water=3/2). The solvent was distilled off under reduced pressure, and the residue was crystallized from ethanol to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[[(4S)-2,2-dimethyl-1,3-dioxolan-4-yl]methyloxycarbonyloxymethyl]-1H-1,2,4-triazolium chloride (Compound 27, 0.4 g) as white crystals.

$^1$H-NMR(d$_6$-DMSO) δ:0.98(3H,d,J=7.0 Hz), 1.26(3H,s), 1.30(3H,s), 3.62–3.72(2H,m), 3.97–4.34(7H,m), 4.70(1H,q, J=7.0 Hz), 4.88(1H,d,J=14.2 Hz), 5.12(1H,d,14.2 Hz), 6.16 (1H,d,J=11.0 Hz), 6.24(1H,d,J=11.0 Hz), 6.66(1H,s), 6.94–7.03(1H,m), 7.21–7.38(2H,m), 7.89(4H,s), 9.10(1H,s), 10.05(1H,s), 10.51(1H,s).

EXAMPLE 35

1-[(2R,3R)-2-(2,4-Difluorophenyl)-2-hydroxy-3-[2-oxo-3-[4-(1H-tetrazol-1-yl)phenyl]-1-imidazolidinyl]butyl]-4-[[(4S)-2,2-dimethyl-1,3-dioxolan-4-yl]methyloxycarbonyloxymethyl]-1H-1,2,4-triazolium chloride (Compound 27, 0.1 g) was dissolved in tetrahydrofuran (1.5 ml), and to the solution was added 1-N hydrochloric acid solution (1.5 ml) under ice cooling. The mixture was stirred for 4 hours at room temperature. The resulting mixture was subjected to ODS column chromatography (eluent: methanol/water=3/2) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[[(2S)-2,3-dihydroxypropoxy]carbonyloxymethyl]-1H-1,2,4-triazolium chloride (Compound 28, 0.05 g) as a white powder.

$^1$H-NMR (d$_6$-DMSO) δ: 0.98 (3H,d,J=7.0 Hz), 3.26–4.24 (9H,m), 4.70 (1H,q, J=7.0 Hz), 4.86 (1H,d,J=14.6 Hz), 5.09 (1H,d,J=14.6 Hz), 6.15 (1H,d,J=11.0 Hz), 6.22 (1H,d,J=11.0 Hz), 6.63 (1H,s), 6.96–7.06 (1H,m), 7.23– 7.36 (2 H,m), 7.90 (4 H,s), 9.10 (1H,s), 10.06 (1H,s), 10.46 (1H,s).

EXAMPLE 36

To a solution of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (1.0 g) in acetonitrile (15 ml) was added (3-benzyloxycarbonylpropyl) iodomethyl carbonate (1.0 g) under a nitrogen atmosphere, and the mixture was stirred for 20 hours at 45–50° C. The reaction mixture was concentrated under reduced pressure. The residue was subjected to silica gel column chromatography (eluent: ethyl acetate→acetone ), and a fraction containing the desired compound was concentrated under reduced pressure. The residue was subjected to ODS column chromatography (eluent: methanol/water=3/2 ) to give 4-[(3-benzyloxycarbonylpropoxy)carbonyloxymethyl]-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium iodide (Compound 32, 1.47 g) as a yellow powder.

$^1$H-NMR (d$_6$-DMSO) δ: 1.04 (3H,d,J=7 Hz), 1.83–1.97 (2H,m), 2.45 (2H,t, J=7 Hz), 3.57–3.69 (2H,m), 3.90–4.09 (2H,m), 4.18 (2H,t, J=7 Hz), 4.69 (1H,q, J=7 Hz), 4.87 (1H,d,J=14 Hz), 4.98 (1H,d,J=14 Hz), 5.08 (2H,s), 6.14 (1H,d,J=11H,z), 6.22 (1H,d,J=11H,z), 6.33 (1H,s), 6.99–7.08 (1H,m), 7.23–7.32 (2H,m), 7.35 (5H,s), 7.91 (4H,s), 9.12 (1H,s), 10.07 (1H,s), 10.24 (1H,s).

EXAMPLE 37

4-[(3-Benzyloxycarbonylpropoxy)carbonyloxymethyl]-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium iodide (Compound 32, 1.47 g) was subjected to ion-exchange chromatography (Dowex 1×8, Cl⁻ type, 500 ml), and a fraction containing the desired product was concentrated under reduced pressure to give 4-[(3-benzyloxycarbonylpropoxy)carbonyloxy-methyl]-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 29, 893 mg) as a white powder.

$^1$H-NMR (d$_6$-DMSO) d:1.04 (3H,d,J=7 Hz), 1.82–1.99 (2H,m), 2.44 (2H,t, J=7 Hz), 3.53–3.67 (2H,m), 3.95–4.03 (2H,m), 4.17 (2H,t, J=7 Hz), 4.68 (1H,q, J=7 Hz), 4.87 (1H,d,J=14 Hz), 5.06 (1H,d,J=14 Hz), 5.07 (2H,s), 6.13 (1H,d,J=11H,z), 6.21 (1H,d,J=11H,z), 6.56 (1H,s), 6.95–7.05 (1H,m), 7.23–7.33 (2H,m), 7.34 (5H,s), 7.90 (4H,s), 9.09 (1H,s), 10.07 (1H,s), 10.41 (1H,s).

EXAMPLE 38

4-[(3-Benzyloxycarbonylpropoxy)carbonyloxymethyl]-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 29, 155 mg) was dissolved in methanol (6 ml). To the solution were added 1N hydrochloric acid solution (0.2 ml) and 10% palladium-carbon (50% wet, 77 mg). The mixture was stirred for 0.5 hours at room temperature under a hydrogen atmosphere. The catalyst was filtered off, and to the filtrate was added distilled water. The mixture was concentrated under reduced pressure, and the concentrate was lyophilized to give 1-[(2R, 3R)-2-(2,4-difluorophenyl)-2-hydroxy-3-[2-oxo-3-[4-(1H-tetrazol-1-yl)phenyl]-1-imidazolidinyl]butyl]-4-[(3-carboxypropoxy)carbonyloxymethyl]-1H-1,2,4-triazolium chloride (Compound 33, 122 mg) as a white powder.

$^1$H-NMR (d$_6$-DMSO) d:0.98 (3H,d,J=7 Hz), 1.78–1.90 (2H,m), 2.29 (2H,t, J=7 Hz), 3.54–3.69 (2H,m), 3.94–4.04 (2H,m), 4.16 (2H,t, J=7 Hz), 4.69 (1H,q, J=7 Hz), 4.87 (1H,d,J=14 Hz), 5.06 (1H,d,J=14 Hz), 6.13 (1H,d,J=11H,z), 6.21 (1H,d,J=11H,z), 6.54 (1H,s), 6.95–7.10 (1H,m), 7.24–7.37 (2H,m), 7.90 (4H,s), 8.31 (1H,s), 9.09 (1H,s), 10.06 (1H,s), 10.34 (1H,s).

EXAMPLE 39

A solution of bromomethyl acetate (2.4 g) and sodium iodide (2.3 g) in acetonitrile (75 ml) was stirred for 2 hours at 80° C. The reaction mixture was cooled to room temperature, and the resulting crystals were filtered off, and to the filtrate was added 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (5 g). The mixture was stirred for 16 hours at 45° C. The precipitates in the reaction mixture were filtered off, and the solvent was distilled off. The residue was dissolved in tetrahydrofuran (150 ml). The solution was washed with a mixture of saturated aqueous solution of sodium chloride (150 ml) and 5% aqueous solution of sodium thiosulfate (10 ml). The organic layer was washed twice with saturated aqueous solution of sodium chloride (150 ml). The tetrahydrofuran layer was dried over anhydrous magnesium sulfate, and the solvent was distilled off. To the residue was added ethanol (50 ml), and solvent was distilled off. To the residue were added acetone (3 ml) and ethanol (1.3 ml), and the mixture was allowed to stand for 2 hours at 0° C. To the resulting white solid was added ethanol (3 ml). The solid was collected by filtration and dried under reduced pressure. The resulting white powder was dissolved in a mixture of tetrahydrofuran (400 ml) and methanol (70 ml). The solution was washed with a saturated aqueous solution of sodium chloride (250 ml) seven times. The organic layer was dried over anhydrous magnesium sulfate and the solvent was distilled off under reduced pressure. The residue was dissolved in a mixture of ethanol (150 ml) and acetone (50 ml), and the solvent was distilled of under reduced pressure. To the residue was added ethanol (100 ml) and the solvent was again distilled off under reduced pressure. To the residue was added a mixture of ethanol (150 ml) and acetone (50 ml). The solvent was distilled off to make the volume of the solution of 20 ml, and the solution was allowed to stand for 2 hours at room temperature. The resulting solid was collected by filtration to give 4-acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 12, 3.6 g) as white crystals. The physicochemical properties of this product were identical with those of the crystals of Compound 12 obtained by crystallization from ethanol in Example 15.

EXAMPLE 40

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (2.0 g) and [2-(acetylamino)ethyl] iodomethyl carbonate (2.9 g) was added acetonitrile (20 ml), and the mixture was stirred for 20 hours at 50~55° C. under an argon atmosphere. The reaction mixture was concentrated under reduced pressure. The residue was dissolved in a mixture of ethyl acetate (100 ml) and tetrahydrofuran (50 ml). To the mixture was added a mixture of saturated aqueous solution of sodium chloride (50 ml) and 5% aqueous solution of sodium thiosulfate (0.1 ml), and the mixture was shaken. The organic layer was washed 4 times with saturated aqueous solution of sodium chloride (50 ml). The organic layer was dried over anhydrous magnesium sulfate, and the solvent was distilled off. The residue was subjected to silica gel flush chromatography (eluent: ethyl acetate→acetone→acetone/ethanol=4/1). The fraction containing the desired compound was concentrated under reduced pressure. The residue was subjected to ODS column chromatography (eluent: methanol/water=3/2), and the eluate was subjected to ion-exchange chromatography (Dowex 1×8, Cl⁻ type). The fraction containing the desired compound was concentrated under reduced pressure to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(2-acetylaminoethoxy)carbonyloxymethyl]-1H-1,2,4-triazolium chloride (Compound 34, 0.50 g) as a white powder.

$^1$H-NMR(d$_6$-DMSO) δ: 0.97(3H,d,J=7 Hz),1.77(3H,s), 3.30(2H,q,J=6 Hz),3.60–3.72(1H,m),3.92–4.08(3H,m),4.12 (2H,t,J=6 Hz),4.65–4.75(1H,m), 4.87(1H,d, J=14 Hz), 5.10 (1H,d,J=14 Hz), 6.14(1H,d,J=11H,z),6.23(1H,d,J=11H,z), 6.63 (1H, s), 6.95–7.05(1H,m), 7.26–7.37(2H,m), 7.90(4H, s), 8.09(1H,t,J=6 Hz), 9.10 (1H,s), 10.07 (1H,s), 10.49(1H, s).

EXAMPLE 41

To a mixture of 1-[(1R,2R)-2-(2,4-difluorophenyl)-2-hydroxy-1-methyl-3-(1H-1,2,4-triazol-1-yl)propyl]-3-[4-(1H-tetrazol-1-yl)phenyl]-2-imidazolidinone (1.0 g) and iodomethyl [3-(methoxy)propyl] carbonate(1.1 g) was added acetonitrile (10 ml), and the mixture was stirred for 15 hours at 40~50° C. under an argon atmosphere. The reaction mixture was concentrated under reduced pressure. The residue was dissolved in a mixture of acetonitrile (5 ml) and ethyl acetate (100 ml). The solution was shaken with a mixture of saturated aqueous solution of sodium chloride (50 ml) and 5% aqueous solution of sodium thiosulfate (0.1 ml). The organic layer was washed four times with saturated aqueous solution of sodium hydrogen chloride (50 ml). The organic layer was dried over anhydrous magnesium sulfate, and the solvent was distilled off under reduced pressure. The residue was subjected to silica gel flush chromatography (eluent: ethyl acetate→acetone→acetone/ethanol=4/1). The fraction containing the desired compound was concentrated under reduced pressure.

The residue was subjected to ion-exchange chromatography (Dowex 1×8, Cl⁻ type), and then the eluate was subjected to ODS column chromatography (eluent: methanol/water=3/2) to give 1-[(2R,3R)-2-(2,4-difluorophenyl)-2-hydroxy-3-[2-oxo-3-[4-(1H-tetrazol-1-yl)phenyl]-1-imidazolidinyl]butyl]-4-[(3-methoxypropoxy)carbonyloxymethyl]-1H-1,2,4-triazolium chloride (Compound 35, 0.80 g) as a white powder.

$^1$H-NMR(d$_6$-DMSO) δ: 0.97(3H,d,J=7 Hz), 1.83(2H, quintet,J=6 Hz), 3.20(3H,s) 3.35(2H,t,J=6 Hz), 3.55–3.70 (1H,m), 3.90–4.10(3H,m), 4.18(2H,t,J=6 Hz), 4.64–4.75 (1H,m), 4.87(1H,d,J=14 Hz), 5.11(1H,d,J=14 Hz), 6.14(1H, d,J=11H,z), 6.22(1H,d,J=11H,z), 6.66(1H,s), 6.95–7.05(1H, m), 7.25–7.39(2H,m), 7.90(4H,s) ,9.10(1H,s), 10.07(1H,s), 10.48(1H,s).

EXAMPLE 42

A solution of bromomethyl acetate (424 mg) and sodium iodide (415 mg) in acetonitrile (15 ml) was stirred for 2 hours at 80° C. The reaction mixture was cooled to room temperature, and residual sodium bromide was filtered off. To the filtrate was added 2-[(1R,2R)-2-(2,4-difluorophenyl)-2-hydroxy-1-methyl-3-(1H-1,2,4-triazol-1-yl)propyl]-4-[4-(2,2,3,3-tetrafluoro-propoxy)phenyl]-3(2H,4H)-1,2,4-triazolone (1 g), and the mixture was stirred for 16 hours at 45° C. The precipitate in the reaction mixture was filtered off, and the solvent was distilled off under reduced pressure. The residue was dissolved in tetrahydrofuran (30 ml), and washed with a mixture of saturated aqueous solution of sodium chloride (30 ml) and 5% aqueous solution of sodium thiosulfate (2 ml), and then washed twice with saturated aqueous solution of sodium chloride (30 ml). The tetrahydrofuran layer was dried over anhydrous magnesium sulfate, and the solvent was distilled off under reduced pressure. The residue was subjected to silica gel chromatography (eluent: ethyl acetate→ethyl acetate/ethanol=10/1→4/1) and then subjected to ion-exchange resin [Dowex 1×8 (Cl⁻ type)) (eluent: water). A fraction containing the desired product was lyophilized to give 4-acetoxymethyl-1-[(2R,3R)-2-(2, 4-difluorophenyl)-2-hydroxy-3-[4,5-dihydro-5-oxo-4-[4-(2, 2,3,3-tetrafluoropropoxy)phenyl]-1H-1,2,4-triazol-1-yl] butyl-1H-1,2,4-triazolium chloride (Compound 36, 294 mg) as a white powder.

$^1$H-NMR(d$_6$-DMSO) δ: 1.22 (3H, d, J=7 Hz), 2.08 (3H, s), 4.66 (2H, t, J=14 Hz), 4.85 (1H, d, J=14 Hz), 4.89 (1H, q, J=7 Hz), 4.98 (1H, d, J=14 Hz), 6.09 (1H, d, J=11H,z), 6.19 (1H, d, J=11H,z), 6.26 (1H, s), 6.69 (1H, tt, J=52, 5 Hz), 6.97–7.06 (1H, m), 7.23 (2H, d, J=9 Hz), 7.25–7.41 (2H, m), 7.69 (2H, d, J=9 Hz), 8.58 (1H, S), 9.09 (1H, s), 10.25 (1H, s).

EXAMPLE 43

A solution of 1-[(1R,2R)-2-(2,4-difluorophenyl)-2-hydroxy-1-methyl-3-(1H-1,2,4-triazol-1-yl)propyl]-3-[4-

(1H-tetrazol-1-yl)phenyl]-2-imidazolidinone (200 mg) and bromomethyl acetate (77.1 mg) in acetonitrile (2 ml) was stirred for 7 hours at 80° C. under an argon atmosphere. The reaction mixture was diluted with acetonitrile (11 ml), and the resulting mixture was stirred at 80° C. until the crystals precipitated in the mixture were dissolved. After having been cooled to room temperature, silica gel (400 mg) was added, and the mixture was stirred for 10 minutes at room temperature. The silica gel was filtered off and washed with a mixture of acetonitrile and tetrahydrofuran (1/1, 2 ml×3). The mother liquor and the washings were combined, and a saturated aqueous solution of sodium chloride (10 ml) was added. The resulting mixture was stirred for 30 minutes at room temperature, and the organic layer was separated. The same operation, the addition of a saturated aqueous of solution of sodium chloride (10 ml) followed by the stirring for 30 minutes at room temperature and the subsequent separation of the organic layer, was further performed three times. The organic layer was dried over anhydrous magnesium sulfate, and the solvent was distilled off under reduced pressure. The residue was dissolved in tetrahydrofuran (3 ml), and the solution was allowed to stand for 5 hours at room temperature. The precipitated solid (179 mg) was collected by filtration and dissolved in a mixture of methanol and tetrahydrofuran (1/1, 4 ml). The solution was concentrated under reduced pressure and the residue was dissolved in tetrahydrofuran (2 ml). The solution was allowed to stand for 5 hours at room temperature. The precipitated powdery crystals (167 mg) was collected by filtration and dissolved in a mixture of ethanol (6 ml) and acetone (0.5 ml). The solution was concentrated under reduced pressure to a volume of ca. 2 ml and allowed to stand for 3 hours at room temperature. The solid precipitated was collected by filtration to give 4-acetoxymethyl-1-[(2R,3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride (Compound 12, 126 mg) as white crystals. The physicochemical properties of this product were identical with those of the crystals of Compound 12 obtained by crystallization from ethanol in Example 15.

Preparation 1

Using the Compound 2 obtained in Example 4, an injection containing the components stated below was prepared.

| | |
|---|---|
| Compound 2 obtained in Example 4 | 100 mg |
| injectable solution of 5% glucose | 100 ml |

Preparation 2

Using the Compound 1 obtained in Example 1, the components stated below were mixed. The mixture was packed in gelatin capsules to obtain capsules, each of which contains the Compound 1 in an amount of 50 mg.

| | |
|---|---|
| Compound 1 | 50 mg |
| Lactose | 100 mg |
| Cornstarch | 40 mg |
| Magnesium stearate | 10 mg |
| Total | 200 mg |

Preparation 3

The compound 2 obtained in Example 4 and magnesium stearate were granulated in an aqueous solution of soluble starch. The resulting product was dried, and then mixed with lactose and cornstarch. The mixture was subjected to compression molding to obtain a tablet containing the components stated below.

| | |
|---|---|
| Compound 2 obtained in Example 4 | 50 mg |
| Lactose | 65 mg |
| Cornstarch | 30 mg |
| Soluble starch | 35 mg |
| Magnesium stearate | 20 mg |
| Total | 200 mg |

Experiment 1

Method: Five-week-old Crj:CDF1 female mice were infected intravenously with minimum lethal dose of *Candida albicans* TA. The test compounds were dissolved in 5% glucose solution and were administered intravenously to the mice immediately after infection. Protective effects of the compounds were expressed as 50% effective dose (ED50) calculated using the method of Reed and Muench from survival rates on day 7 after infection.

Result: The protective effects of the compounds against experimental infection in mice are shown in Table 5.

TABLE 5

| Compound | ED50 ($\mu$mol/kg)i.v. |
|---|---|
| 1 | 2.3 |
| 2 | 1.5 |

Experiment 2

Method: Five-week-old Crj:CDF1 female mice were infected intravenously with minimum lethal dose of *Candida albicans* TA. The test compounds were dissolved in 5% glucose solution and were administered orally to the mice immediately after infection. Protective effects of the compounds were expressed as 50% effective dose (ED50) calculated using the method of Reed and Muench from survival rates on day 7 after infection.

Result: The protective effects of the compounds against experimental infection in mice are shown in Table 6.

TABLE 6

| Compound | ED50 ($\mu$mol/kg)p.o. |
|---|---|
| 1 | 2.9 |
| 2 | 1.8 |

Experiment 3

Method: Five-week-old Crj:CDF1 female mice were infected intravenously with minimum lethal dose of *Candida albicans* T.A. The test compounds were dissolved in 5% glucose solution and were administered intravenously (i.v.) or orally (p.o.) to the mice at a dose of 1.04 $\mu$mol/kg immediately after infection. Protective effect of each compound were expressed as the number of survivors on day 7 after infection and the mean survival days of the mice which had died up to 7 days after infection.

Result: The protective effects of the compounds against experimental infection in mice are shown in Table 7. The protective effect of the reference compound shown in figure (V) is included in Table 7. The reference compound was suspended in 0.5% sodium carboxymethyl cellulose and was administered orally to the mice at a dose of 1.04 $\mu$mol/kg immediately after infection.

TABLE 7

(V)

[Chemical structure of reference compound V: triazole-CH₂-C(OH)(2,4-difluorophenyl)-CH(CH₃)-N connected to imidazolidinone-phenyl-tetrazole, with (R)(R) stereochemistry]

Protective effect at a dose of 1.04 μmol/kg (n = 5)
No. of survivors
(Mean survival day of the mice which died)

| Compound | i. v. | p. o. |
|---|---|---|
| None | 0 (0.8) | |
| Reference compound (V) | — | 2 (4.3) |
| The compound of the invention | | |
| 11 | 2 (4.0) | 3 (6.0) |
| 12 | 3 (4.5) | 4 (5.0) |
| 14 | 1 (4.5) | 3 (6.0) |
| 16 | 4 (6.0) | 5 |
| 18 | 3 (5.5) | 3 (4.5) |

Industrial Applicability

The compounds of the present invention have an improved solubility in water, and can advantageously be applied to injection, and further have an improved internal absorption. Thus the compounds of the present invention can be expected to have a good effect for the treatment of disease.

Figure 1:
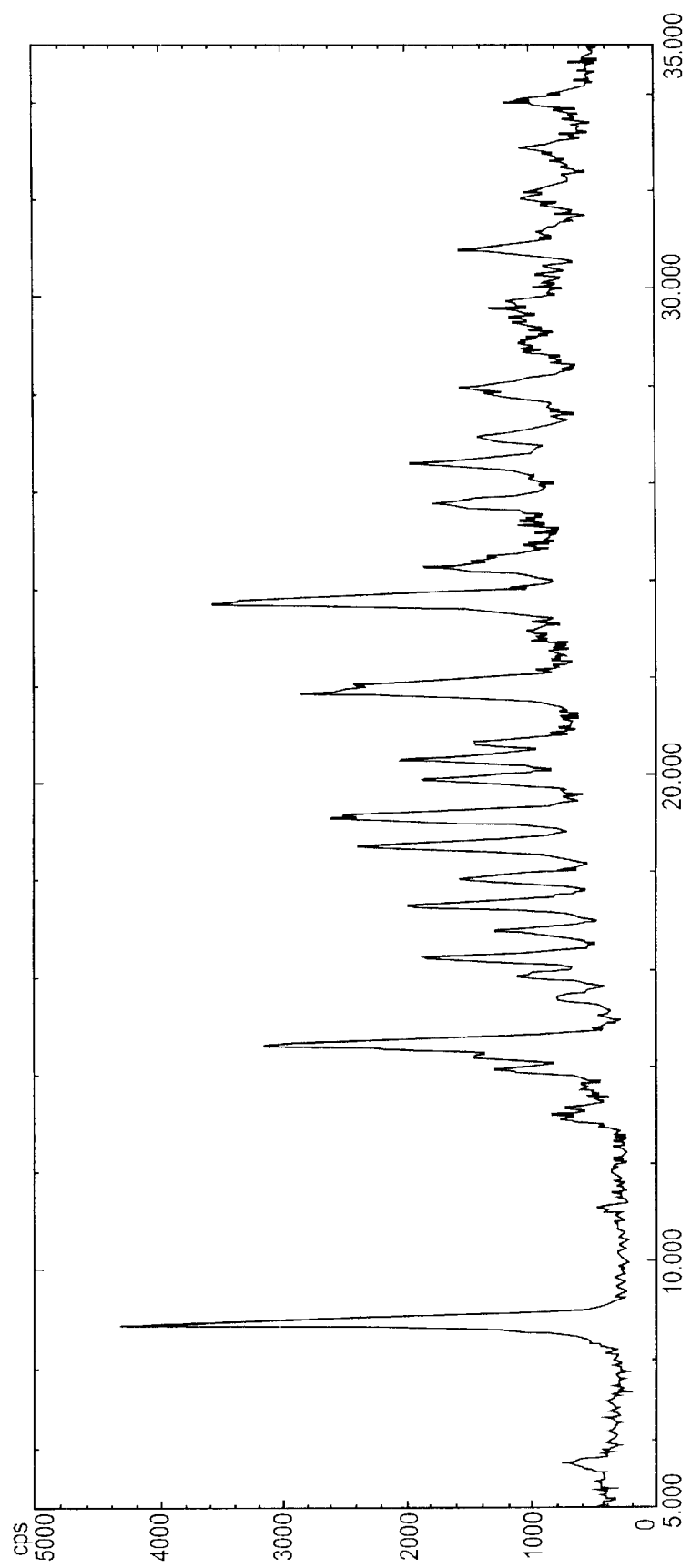
[FIG. 1] shows a powder X-ray diffraction spectrum (Cu, 40 kV, 50 mA) of Form I crystals (non-hydrate, crystallized from ethanol) of Compound 12 produced in Example 15. Transverse axis shows angle of diffraction (2θ), and ordinate axis shows peak strength.
Figure 2:
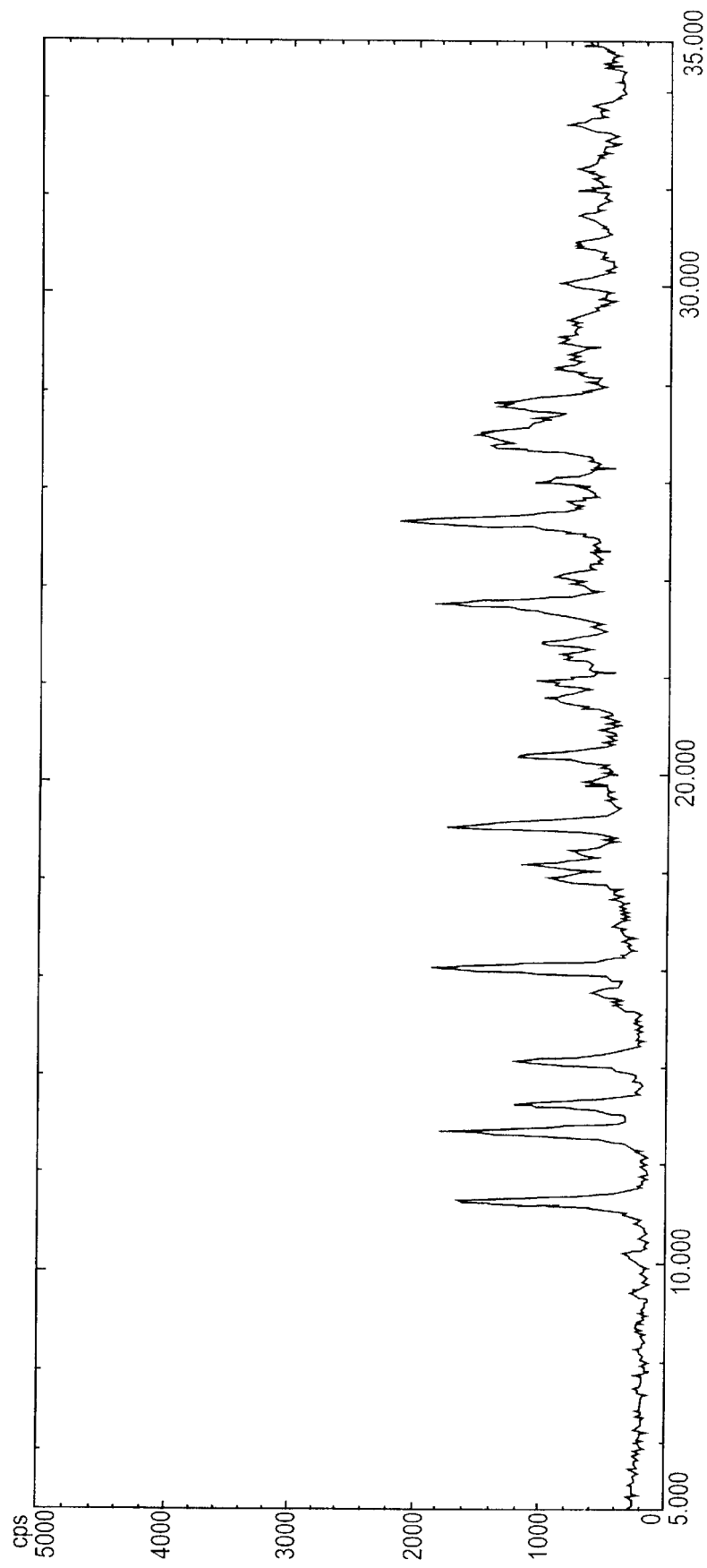
[FIG. 2] shows a powder X-ray diffraction spectrum (Cu, 40 kV, 50 mA) of Form II crystals (hydrate, crystallized from water) of Compound 12 produced in Example 15. Transverse axis shows angle of diffraction (2θ), and ordinate axis shows peak strength.

What is claimed is:

1. 4-acetoxymethyl-1-[(2R, 3R)-2-(2,4-difluorophenyl)-2-hydroxy-3-[2-oxo-3-[4-(1H-tetrazol-1-yl)phenyl]-1-imidazolidinyl]butyl]-1H-1,2,4-triazolium chloride.

2. A pharmaceutical composition comprising 4-acetoxymethyl-1-[(2R,3R)-2-(2,4-difluorophenyl)-2-hydroxy-3-[2-oxo-3-[4-(1H-tetrazol-1-yl)]phenyl]-1-imidazolidinyl]butyl]-1H-1,2,4-triazolium chloride and at least one of a pharmaceutically acceptable carrier, diluent or excipient.

3. A method for treating fungal infection comprising administering an effective amount of 4-acetoxymethyl-1-[(2R,3R)-2-(2,4-difluorophenyl)-2-hydroxy-3-[2-oxo-3-[4-(1H-tetrazol-1-yl)]phenyl]-1-imidazolidinyl]butyl]-1H-1,2,4-triazolium chloride optionally together with a pharmaceutically acceptable carrier, diluent or excipient to a patient suffering from fungal infection.

4. The pharmaceutical composition of claim 2 wherein said composition is injectable.

5. The method of claim 3 wherein 4-acetoxymethyl-1-[(2R,3R)-2-(2,4-difluorophenyl)-2-hydroxy-3-[2-oxo-3-[4-(1H-tetrazol-1-yl)]phenyl]-1-imidazolidinyl]butyl]-1H-1,2,4-triazolium chloride optionally together with a pharmaceutically acceptable carrier, diluent or excipient is administered by injection.

* * * * *